US011224683B2

(12) United States Patent
Karoor

(10) Patent No.: US 11,224,683 B2
(45) Date of Patent: *Jan. 18, 2022

(54) SYSTEM FOR REMOVING UREMIC TOXINS IN DIALYSIS PROCESSES

(71) Applicants: Baxter International Inc., Deerfield, IL (US); Baxter Healthcare SA, Glattpark (CH)

(72) Inventor: Sujatha Karoor, Lake Forest, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 83 days.

This patent is subject to a terminal disclaimer.

(21) Appl. No.: 16/661,613

(22) Filed: Oct. 23, 2019

(65) Prior Publication Data

US 2020/0054812 A1 Feb. 20, 2020

Related U.S. Application Data

(60) Continuation of application No. 16/366,195, filed on Mar. 27, 2019, now Pat. No. 10,493,193, which is a (Continued)

(51) Int. Cl.
*A61M 1/16* (2006.01)
*A61M 1/28* (2006.01)
(Continued)

(52) U.S. Cl.
CPC .......... *A61M 1/1696* (2013.01); *A61M 1/14* (2013.01); *A61M 1/1694* (2013.01);
(Continued)

(58) Field of Classification Search
CPC .... A61M 1/14; A61M 1/1696; A61M 1/3679; A61M 1/3687; A61M 1/267; A61M 1/28;
(Continued)

(56) References Cited

U.S. PATENT DOCUMENTS

| 7,241,272 B2 | 7/2007 | Karoor et al. |
| 2005/0006296 A1 | 1/2005 | Sullivan et al. |
| 2011/0171713 A1 | 7/2011 | Bluchel et al. |

FOREIGN PATENT DOCUMENTS

| CN | 1596136 | 3/2005 |
| CN | 101784292 | 7/2010 |
| WO | 03/041764 | 5/2003 |

OTHER PUBLICATIONS

Chinese Office Action for Chinese Application No. 201380014561.0, dated Oct. 8, 2015.
(Continued)

*Primary Examiner* — John Kim
(74) *Attorney, Agent, or Firm* — K&L Gates LLP

(57) ABSTRACT

A method of performing dialysis includes: recirculating a dialysis fluid from a patient or a dialyzer for at least two cycles, each cycle contacting the dialysis fluid first with a zirconium phosphate layer followed by at least one of a urease layer, a zirconium oxide layer, or a carbon layer; storing the recirculated dialysis fluid in a storage container; and transferring the dialysis fluid from the storage container to the patient or the dialyzer. In one example, the zirconium phosphate layer and the at least one of the urease layer, the zirconium oxide layer, or the carbon layer is provided by a sorbent cartridge.

10 Claims, 25 Drawing Sheets

Related U.S. Application Data continuation of application No. 16/134,439, filed on Sep. 18, 2018, now Pat. No. 10,272,189, which is a division of application No. 14/989,239, filed on Jan. 6, 2016, now Pat. No. 10,112,001, which is a continuation of application No. 13/745,388, filed on Jan. 18, 2013, now Pat. No. 9,242,035.

(60) Provisional application No. 61/588,479, filed on Jan. 19, 2012.

(51) Int. Cl.
| | | |
|---|---|---|
| *A61M 1/26* | (2006.01) | |
| *A61M 1/36* | (2006.01) | |
| *B01J 20/02* | (2006.01) | |
| *B01J 20/06* | (2006.01) | |
| *B01J 20/20* | (2006.01) | |
| *B01J 20/28* | (2006.01) | |
| *A61M 1/14* | (2006.01) | |
| *B01J 20/24* | (2006.01) | |

(52) U.S. Cl.
CPC .............. *A61M 1/267* (2014.02); *A61M 1/28* (2013.01); *A61M 1/284* (2014.02); *A61M 1/287* (2013.01); *A61M 1/3679* (2013.01); *A61M 1/3687* (2013.01); *B01J 20/0292* (2013.01); *B01J 20/06* (2013.01); *B01J 20/20* (2013.01); *B01J 20/24* (2013.01); *B01J 20/28052* (2013.01); *A61M 2209/088* (2013.01); *B01J 2220/62* (2013.01)

(58) Field of Classification Search
CPC .... A61M 1/1694; A61M 1/284; A61M 1/287; A61M 2209/088; B01J 20/06; B01J 20/0292; B01J 20/20; B01J 20/28052; B01J 20/24; B01J 2220/62
See application file for complete search history.

(56) References Cited

OTHER PUBLICATIONS

International Search Report for International Application No. PCT/US2013/022193, dated Apr. 5, 2013.
International Preliminary Report on Patentability for International Application No. PCT/US2013/022193, dated Jul. 22, 2014.

SYSTEM FOR REMOVING UREMIC TOXINS IN DIALYSIS PROCESSES

PRIORITY CLAIM

This application is a continuation of U.S. patent application Ser. No. 16/366,195, filed on Mar. 27, 2019, now U.S. Pat. No. 10,493,193, which is a continuation of U.S. patent application Ser. No. 16/134,439, filed on Sep. 18, 2018, now U.S. Pat. No. 10,272,189, which is a divisional of U.S. patent application Ser. No. 14/989,239, filed on Jan. 6, 2016, now U.S. Pat. No. 10,112,001, which is a continuation of U.S. patent application Ser. No. 13/745,388, filed on Jan. 18, 2013, now U.S. Pat. No. 9,242,035, which application claims priority to U.S. Provisional Patent Application No. 61/588,479, filed Jan. 19, 2012, the entire contents of each of which are incorporated herein by reference.

CROSS-REFERENCE TO RELATED APPLICATIONS

This application is related in subject matter to Patent Cooperation Treaty Application WO 2007/089855 A2, the entire contents of which are incorporated herein by reference and relied upon.

BACKGROUND

The present disclosure relates generally to methods of treatment. More specifically, the present disclosure relates to dialysis processes.

Due to disease or insult or other causes, the renal system can fail. In renal failure of any cause, there are several physiological derangements. The balance of water, minerals (Na, K, Cl, Ca, P, Mg, $SO_4$) and the excretion of daily metabolic load of fixed hydrogen ions is no longer possible in renal failure. During renal failure, toxic end products of nitrogen metabolism (urea, creatinine, uric acid, and others) can accumulate in blood and tissues.

Dialysis processes have been devised for the separation of elements in a solution by diffusion across a semi-permeable membrane (diffusive solute transport) down a concentration gradient. Principally, dialysis comprises two methods: hemodialysis and peritoneal dialysis.

Hemodialysis treatment utilizes the patient's blood to remove waste, toxins, and excess water from the patient. The patient is connected to a hemodialysis machine and the patient's blood is pumped through the machine. Catheters are inserted into the patient's veins and arteries to connect the blood flow to and from the hemodialysis machine. Waste, toxins, and excess water are removed from the patient's blood and the blood is infused back into the patient. Hemodialysis treatments last several hours and are generally performed in a treatment center about three or four times per week.

Peritoneal dialysis utilizes a dialysis solution and dialysate, which is infused into a patient's peritoneal cavity. The dialysate contacts the patient's peritoneal membrane in the peritoneal cavity. Waste, toxins, and excess water pass from the patient's bloodstream through the peritoneal membrane and into the dialysate. The transfer of waste, toxins, and water from the bloodstream into the dialysate occurs due to diffusion and osmosis. The spent dialysate is drained from the patient's peritoneal cavity to remove the waste, toxins, and water from the patient.

There are various types of peritoneal dialysis, including continuous ambulatory peritoneal dialysis (CAPD) and automated peritoneal dialysis (APD). CAPD is a manual dialysis treatment in which the patient connects an implanted catheter to a drain and allows a spent dialysate fluid to drain from the peritoneal cavity. The patient then connects to a bag of fresh dialysate and manually infuses the fresh dialysate through the catheter and into the patient's peritoneal cavity. The patient disconnects the catheter from the fresh dialysate bag and allows the dialysate to dwell within the cavity to transfer waste, toxins, and excess water from the patient's bloodstream to the dialysate solution. After the dwell period, the patient repeats the manual dialysis procedure.

In CAPD the patient performs several drain, fill, and dwell cycles during the day, for example, about four times per day. Each treatment cycle typically takes about 3-4 hours. Manual peritoneal dialysis performed by the patient requires a great deal of time and effort by the patient. The patient is routinely inconvenienced leaving ample opportunity for therapy enhancements to improve patient quality of life.

Automated peritoneal dialysis is similar to continuous peritoneal dialysis in that the dialysis treatment includes a drain, fill, and dwell cycle. However, a dialysis machine automatically performs 3-4 cycles of peritoneal dialysis treatment, typically overnight while the patient sleeps.

To this end, a dialysis machine is fluidly connected to an implanted catheter. The dialysis machine is also fluidly connected to a source of fresh dialysate, such as a bag of dialysate solution, and to a fluid drain. The dialysis machine pumps spent dialysate from the peritoneal cavity though the catheter to the drain. Then, the dialysis machine pumps fresh dialysate from the dialysate source through the catheter and into the patient's peritoneal cavity. The dialysis machine allows the dialysate to dwell within the cavity to transfer waste, toxins, and excess water from the patient's bloodstream to the dialysate solution. The dialysis machine is computer controlled so that the dialysis treatment occurs automatically when the patient is connected to the dialysis machine, for example, overnight.

Several drain, fill, and dwell cycles will occur during the treatment. Also, a last fill is typically used at the end of the automated dialysis treatment so that the patient can disconnect from the dialysis machine and continue daily functions while dialysate remains in the peritoneal cavity. Automated peritoneal dialysis frees the patient from manually performing the drain, dwell, and fill steps, and can improve the patient's dialysis treatment and quality of life.

In view of recent developments and therapies, the line between traditional peritoneal dialysis and hemodialysis has become blurred. For example, some therapies use components of both therapies.

A recent therapy is regenerative dialysis. In this system a dialysis system is used that includes a cartridge for dialysate regeneration. The cartridge includes a resin bed including zirconium-based resins. An example of a cartridge that is used in such a system is manufactured under the name Redy by Sorb Technology, Oklahoma City, Okla. This system, however, requires the constant attention of medical personnel. Moreover, the dialysate that is regenerated by the cartridge has an undesirable sodium and pH level. In this regard, the dialysis solution does not have a physiologic pH or electrolyte content. This is especially a problem if the dialysis solution is to be reinfused into the peritoneal cavity of a patient.

SUMMARY

The present disclosure provides improved systems as well as methods for providing dialysis to a patient. More specifically, in an embodiment, the present disclosure provides systems, cartridges, and methods for regenerative dialysis therapies. However, it should be noted that the cartridge of the present disclosure can be used in a variety of therapies including hemodialysis and peritoneal dialysis therapies as well as acute dialysis. The cartridge of the present disclosure is suitable for use in portable (e.g., wearable) systems or in conventional systems typically found, for example, in a clinic setting.

To this end, in an embodiment, a device for removing uremic toxins in a dialysis procedure is provided comprising a body having an inlet and an outlet and defining an interior, the interior including a layer comprising urease, a layer comprising zirconium oxide, a layer comprising zirconium phosphate, and a layer comprising carbon, and the device being so constructed and arranged so that a fluid entering the device contacts the zirconium oxide layer upon entering the device before contacting the urease or the zirconium phosphate layer.

In an embodiment, the zirconium oxide is in bicarbonate form.

In an embodiment, the zirconium oxide is in hydroxyl form.

In an embodiment, the carbon layer is located in juxtaposition to the outlet.

In an embodiment, the fluid flows through a layer of zirconium oxide before entering the carbon layer.

In an embodiment, the zirconium phosphate has a pH of approximately 2 to about 8.

In an embodiment, the zirconium oxide has a pH of approximately 6 to about 13.

In an embodiment, two separate layers of zirconium phosphate are provided.

In an embodiment, two separate layers of zirconium oxide are provided.

In an embodiment, open headers at each of the inlet and outlet end of the device are provided.

In an embodiment, an opening for venting a gas to the atmosphere located at the outlet end is provided.

In an embodiment the urease layer is the first layer.

In an embodiment the zirconium phosphate layer is located before the zirconium oxide layer.

In a further embodiment of the present disclosure, a cartridge for use in a dialysis system for removing toxins is provided comprising a body having an inlet end and an outlet end. The body includes an interior including at least four layers, the layers including a first layer of a resin selected from the group consisting of zirconium phosphate having a pH of approximately 2.5 to about 5 and urease, a second layer of a resin selected from the group consisting of zirconium oxide having a pH of approximately 9 to about 13 and urease, a third layer of zirconium phosphate, and a fourth layer of zirconium oxide having a pH of approximately 6.5 to about 7.5. The interior is so constructed and arranged that a fluid entering the interior from the first inlet end flows through the first layer, then the second layer, then the third layer, and then the fourth layer.

In an embodiment, the first layer comprises approximately 200 to about 800 grams of zirconium phosphate.

In an embodiment, the fourth layer comprises approximately 50 to about 200 grams of carbon.

In an embodiment, the urease is a cross-linked enzyme.

In yet another embodiment, a device for regenerating a dialysis solution is provided. The device includes a body including a resin bed. The resin bed includes at least a layer of urease, zirconium phosphate, zirconium oxide, and carbon and being so constructed and arranged that a dialysis solution having a pH that is either basic or acidic will exit the cartridge after it passes through the resin bed at a pH of approximately 7 to about 7.8.

In an embodiment, the first layer of the resin bed that the solution contacts is selected from the group consisting of zirconium phosphate having a pH of approximately 2.0 to about 5 and urease.

In an embodiment, the second layer that the solution passes through in the resin bed is selected from the group consisting of zirconium oxide having a pH of approximately 9 to about 13 and urease.

In an embodiment, the third layer of the resin bed that the solution passes through is zirconium phosphate.

In an embodiment, the fourth layer of the cartridge that the solution passes through is zirconium oxide having a pH of approximately 6.8 to about 7.5.

In an embodiment, the pH of the solution exiting the cartridge is approximately 7.4.

In a further embodiment, a device for use in a system for treating a patient with a dialysis solution is provided. The device including an inlet in fluid communication with a source of dialysis solution, a body including the inlet and defining an interior and having an outlet, and the body including a resin bed including a layer of urease, a layer of zirconium oxide, and a layer of zirconium phosphate that define a three layer structure. The resin bed is oriented so that the first layer that the dialysis solution contacts of the three layer structure is either the urease or the zirconium phosphate layer and the zirconium oxide layer is so constructed and arranged that a basic or an acidic dialysis solution entering the inlet will exit the outlet with a physiologically acceptable pH.

In an embodiment, the device is used in a regenerative dialysis system.

Still further, in an embodiment, a method for constructing a cartridge for use in a system for providing dialysis is provided. The method comprising the steps of providing a resin bed including zirconium oxide and zirconium phosphate and selecting and orienting the zirconium oxide and zirconium phosphate to allow the cartridge to remove uremic toxins present in a dialysis solution entering the resin bed and causing the dialysis solution exiting the cartridge to be at a physiological pH and include a physiological electrolyte balance.

In an embodiment, the method includes the steps of providing a body having an inlet and an outlet and defining an interior, the interior including a layer comprising urease, a layer comprising zirconium oxide, a layer comprising zirconium phosphate, and a layer comprising carbon; and the device being so constructed and arranged so that a fluid entering the device contacts the zirconium phosphate layer upon entering the device before contacting the urease on the zirconium oxide layer.

In a yet further embodiment, a method for providing dialysis is provided comprising the steps of removing uremic toxins by passing a dialysis fluid through a body having an inlet and an outlet and defining an interior, the interior including at least four layers, a first layer comprising either zirconium phosphate having a pH of approximately 2.5 to about 5 or urease, a second layer comprising either zirconium oxide having a pH of approximately 9 to about 13 or urease, a third layer comprising zirconium phosphate and a fourth layer comprising zirconium oxide having a pH of approximately 6.8 to about 7.5.

Additionally, in an embodiment, a method of providing regenerative dialysis is provided comprising the step of removing uremic toxins by passing a dialysis fluid through a body having an inlet and an outlet and defining an interior, the interior including at least four layers, a first layer comprising either zirconium phosphate having a pH of approximately 2.5 to about 5 or urease, a second layer comprising either zirconium oxide having a pH of approximately 9 to about 13 or urease, a third layer comprising zirconium phosphate and a fourth layer comprising zirconium oxide having a pH of approximately 6.8 to about 7.5.

An advantage of the present disclosure is to provide an improved dialysis procedure.

Moreover, an advantage of the present disclosure is to provide an improved cartridge for removing impurities from a dialysis fluid.

Still, an advantage of the present disclosure is to provide an improved system for providing dialysis.

Further, an advantage of the present disclosure is to provide an improved cartridge that can be used in a single loop or multiple loop system.

Additionally, an advantage of the present disclosure is to provide an improved resin bed for a cartridge for a dialysis system.

Additionally, an advantage of the present disclosure is to provide an improved cartridge that is constructed and arranged so that dialysis solution that exits the cartridge has a physiological pH and electrolyte content.

Further, in a first embodiment, the present disclosure provides a system for dialysis, hemofiltration, hemodiafiltration or peritoneal dialysis. The system includes a sorbent cartridge in fluid communication with at least one of a patient or a dialyzer. The sorbent cartridge includes a housing including a zirconium phosphate layer followed by at least one of a urease layer, a zirconium oxide layer, or a carbon layer. A storage container and a pump is in fluid communication with the sorbent cartridge. A control unit is in communication with the pump. The control unit is configured to cause a dialysis fluid flow into the sorbent cartridge in a first direction in which the zirconium phosphate layer is first contacted by the dialysis fluid flow before the urease layer, zirconium oxide layer or carbon layer. The control unit is further configured to cause the dialysis fluid to flow in a second direction that is a reverse direction of the first direction. Here, the layers are contacted in a reverse order, e.g., carbon, zirconium oxide, urease, then the initial zirconium phosphate layer.

In a second embodiment, the present disclosure provides a method of performing hemodialysis, hemofiltration, hemodiafiltration or peritoneal dialysis. The method includes passing a dialysis fluid in a first flow direction through a sorbent cartridge in fluid communication with at least one of a patient or a dialyzer. The sorbent cartridge includes a housing including a zirconium phosphate layer followed by at least one of a urease layer, a zirconium oxide layer, or a carbon layer, wherein the zirconium phosphate layer is first contacted by the dialysis fluid before the urease layer. The method further comprises storing the dialysis fluid in a storage container. The dialysis fluid from the storage container can then be passed back through the sorbent cartridge in a reverse flow direction from the first flow direction to reach the patient or the dialyzer. The dialysis fluid thus flows back through, for example, the carbon layer first, the zirconium oxide second, the urease third and the zirconium phosphate last. As a result, any ammonium in solution at this time will be absorbed by the zirconium phosphate layer in the sorbent cartridge. An infusion solution can be used to replenish the cleaned dialysis fluid with the necessary electrolytes, glucose and modify the pH of the dialysis fluid prior to being transferred back to the patient or dialyzer.

In a third embodiment, the present disclosure provides a system for hemodialysis, hemofiltration, hemodiafiltration or peritoneal dialysis. The system includes a sorbent cartridge in fluid communication with at least one of a patient or a dialyzer. The sorbent cartridge includes a housing including a zirconium phosphate later followed by at least one of a urease layer, a zirconium oxide layer, or a carbon layer. The system also includes a pump and a storage container in fluid communication with the sorbent cartridge and the patient or dialyzer. A control unit is in operable communication with the pump. The control unit is configured to recirculate a dialysis fluid into the sorbent cartridge in a first direction wherein the zirconium phosphate layer is first contacted by the dialysis fluid before the urease layer for at least two cycles followed by storing of the dialysis fluid in the storage container. The control unit can then cause the pump to store fluid to the patient or dialyzer.

In a fourth embodiment, the present disclosure provides a method of performing hemodialysis, hemofiltration, hemodiafiltration or peritoneal dialysis. The method includes passing a dialysis fluid through a sorbent cartridge in fluid communication with at least one of a patient or a dialyzer for at least two cycles. The sorbent cartridge includes a housing including a zirconium phosphate layer followed by at least one of a urease layer, a zirconium oxide layer, or a carbon layer. The zirconium phosphate layer is first contacted by the dialysis fluid before the urease layer. The method further includes storing the dialysis fluid in a storage container. The dialysis fluid from the storage container can then be transferred to reach the patient or the dialyzer. An infusion solution can be used to replenish the cleaned dialysis fluid with the necessary electrolytes, glucose and modify the pH of the dialysis fluid prior to being transferred back to the patient or dialyzer. In each of the above primary embodiments, the control unit cycles or sequences one or more valves to control fluid flow and direction. Examples of specific sequences are shown below.

In a general embodiment illustrated in FIG. 16, the present disclosure provides a system for dialysis, hemofiltration and/or hemodiafiltration. The system can be used for any suitable dialysis therapies including peritoneal dialysis, hemodialysis, hemofiltration, hemodiafiltration, etc.

The system comprises a sorbent cartridge in fluid communication with at least one of a patient or a dialyzer. The sorbent cartridge comprises a housing including a zirconium phosphate layer followed by at least one of a urease layer, a zirconium oxide layer, or a carbon layer. Representative examples of the sorbent cartridge are shown in FIGS. 18*a* and 18*b*. In some configurations, the sorbent cartridge includes a second zirconium phosphate layer. In other configurations, the sorbent cartridge includes a urease layer followed by at least one of a second zirconium layer, a zirconium oxide layer and a carbon layer. In still other configurations, the sorbent cartridge includes a second zirconium phosphate layer, a urease layer disposed between the zirconium phosphate layer and the second zirconium phosphate layer, a zirconium oxide layer disposed adjacent to the second zirconium phosphate layer, and a carbon layer disposed adjacent to the zirconium oxide layer.

A storage container is in fluid communication with the sorbent cartridge. A pump can be used to move a fluid such as a spent dialysis fluid from the patient or dialyzer through the sorbent cartridge to the storage container and back to the patient or dialyzer.

A control unit is in communication with the sorbent cartridge, the storage container, the infusion solution, and the pump. The control system is configured to cause a dialysis fluid flow into the sorbent cartridge in a first direction wherein the zirconium phosphate layer is first contacted by the dialysis fluid flow before the urease layer. The dialysis fluid can then pass through the urease layer to convert the urea to ammonium. The dialysis fluid can then pass through the zirconium oxide layer and the carbon layer to remove additional electrolytes and waste compounds. After the first pass through the sorbent cartridge, the dialysis fluid can be stored in the storage container for a desired amount of time. In configurations including first and second zirconium phosphate layers and a urease layer, the control unit can be programmed to cause the pump to pump the fluid to flow (i) in the first direction through the sorbent cartridge, wherein the first zirconium phosphate layer is contacted by the fluid before the urease layer and the second zirconium phosphate layer, and (ii) in the second direction, reverse from the first direction, through the sorbent cartridge wherein the second zirconium phosphate layer and the urease layer are contacted by the dialysis fluid before the first zirconium phosphate layer.

The control system is further configured to cause the dialysis fluid to flow in a second direction that is a reverse direction of the first direction. In this regard, dialysis fluid from the storage container is passed through the sorbent cartridge in the opposite direction as the first direction. As a result, any ammonium in solution at this time will be absorbed by the zirconium phosphate layer in the sorbent cartridge.

The pump can be any suitable type of pump including, for example, a reversible pump such as a peristaltic pump. The pump may alternatively be a membrane pump which includes a first valve located on a first side of the membrane pump and a second valve located on a second side of the membrane pump. In such a configuration, the control unit is programmed to switch states of the first and second valves in conjunction with the operation of the membrane pump in order to move the fluid (such as a spent dialysis fluid) from the patient or dialyzer through the sorbent cartridge to the storage container and back to the patient or dialyzer.

The system may include one or more valves between the storage container and the patient or dialyzer. The control unit can thus be further programmed to operate the one or more valves and the pump to move the fluid (such as a spent dialysis fluid) from the patient or dialyzer through the sorbent cartridge to the storage container and back to the patient or dialyzer.

An infusion solution can be in fluid communication with the patient or dialyzer. Prior to entering the patient or dialyzer, the infusion solution can be used to replenish the cleaned dialysis fluid with the necessary electrolytes (e.g., calcium, magnesium, etc.) glucose and modify the pH of the dialysis fluid prior before being transferred back to the patient or dialyzer. The control unit can be programmed to cause the infusion solution to be metered into the dialysis fluid while the dialysis fluid is caused to flow in the second direction. The dialysis system can include a second pump, controlled by the control unit, for metering the infusion solution.

The dialysis system can include a heater such as an inline heater or a batch heater operable with the storage container.

The control system can include sensors (pH, electrolyte, conductivity, glucose, temperature etc.) to monitor the physical/chemical properties of the dialysis fluid leaving and entering the patient. The control system can further include the necessary battery/power components, controls, and processors to control the different components of the dialysis system in order to operate the dialysis system as described above.

In another general embodiment shown in FIG. 17, the present disclosure provides a system for dialysis, hemofiltration and/or hemodiafiltration. The system can be used for any suitable dialysis therapy including peritoneal dialysis, hemodialysis, hemofiltration, hemodiafiltration, etc. The system comprises a sorbent cartridge in fluid communication with at least one of a patient or a dialyzer. The sorbent cartridge comprises a housing including a zirconium phosphate later followed by at least one of a urease layer, a zirconium oxide layer, or a carbon layer. Representative examples of the sorbent cartridge are shown in FIGS. 18a and 18b. The system also comprises a storage container and an infusion solution in fluid communication with the sorbent cartridge and the patient or dialyzer. A pump can be used to move a fluid such as a spent dialysis fluid from the patient or dialyzer through the sorbent cartridge to the storage container and back to the patient or dialyzer.

A control system is in communication with the sorbent cartridge, the storage container, the infusion solution, and the pump. The control system is configured to recirculate a spent dialysis fluid into the sorbent cartridge in a first direction wherein the zirconium phosphate layer is first contacted by the dialysis fluid before the urease layer for at least two or more cycles followed by storing of the dialysis fluid in the storage container. A cycle refers to a specific volume of water that passes through the sorbent cartridge at least once.

The number of cycles will be determined by the level of ammonium in the dialysis fluid. There should be a sufficient number of cycles so that the ammonium level is below a threshold level for patient safety (e.g., 20 ppm). After the dialysis fluid is below the threshold level, the cleansed dialysis fluid can be stored in the storage container for a desired amount of time.

After the desired time, the dialysis fluid from the storage container can then be transferred back to the patient or the dialyzer. Prior to entering the patient or dialyzer, the infusion solution can be used to replenish the cleaned dialysis fluid with the necessary electrolytes (e.g., calcium, magnesium, etc.) glucose and modify the pH of the dialysis fluid before being transferred back to the patient or dialyzer.

The control system can include sensors (pH, electrolyte, conductivity, glucose, temperature etc.) to monitor the physical/chemical properties of the dialysis fluid leaving and entering the patient. The control system can further include the necessary battery/power components, controls, and processors to control the different components of the dialysis system in order to operate the dialysis system as described above.

In another general embodiment, the present disclosure provides a system for dialysis, hemofiltration and/or hemodiafiltration. The system can be used for any suitable dialysis therapies including peritoneal dialysis, hemodialysis, hemofiltration, hemodiafiltration, etc.

The system comprises a sorbent cartridge in fluid communication with at least one of a patient or a dialyzer. The sorbent cartridge comprises a housing including a urease layer followed by a zirconium phosphate layer. In some configurations, the sorbent cartridge includes a second zirconium phosphate layer. In other configurations, the sorbent cartridge includes a urease layer followed by a zirconium phosphate layer, followed by at least one of a second zirconium phosphate layer, a zirconium oxide layer and a carbon layer. In still other configurations, the sorbent cartridge does not include a second zirconium phosphate layer.

A storage container is in fluid communication with the sorbent cartridge. A pump can be used to move a fluid such as a spent dialysis fluid from the patient or dialyzer through the sorbent cartridge to the storage container and back to the patient or dialyzer.

A control unit is in communication with the sorbent cartridge, the storage container, the infusion solution, and the pump. The control system is configured to cause a dialysis fluid flow into the sorbent cartridge in a first direction wherein the urease layer is first contacted by the dialysis fluid flow before the zirconium phosphate layer. The dialysis fluid can pass through the urease layer to convert the urea to ammonium. The dialysis fluid can then pass through an optional zirconium oxide layer and/or an optional carbon layer to remove additional electrolytes and waste compounds. After the first pass through the sorbent cartridge, the dialysis fluid can be stored in the storage container for a desired amount of time. In configurations including first and second zirconium phosphate layers and a urease layer, the control unit can be programmed to cause the pump to pump the fluid to flow (i) in the first direction through the sorbent cartridge, wherein the urease layer is contacted by the fluid before the first zirconium phosphate layer and the second zirconium phosphate layer, and (ii) in the second direction, reverse from the first direction, through the sorbent cartridge wherein the first zirconium phosphate layer and the second zirconium phosphate layer are contacted by the dialysis fluid before the urease layer.

The control system is further configured to cause the dialysis fluid to flow in a second direction that is a reverse direction of the first direction. In this regard, dialysis fluid from the storage container is passed through the sorbent cartridge in the opposite direction as the first direction. As a result, any ammonium in solution at this time will be absorbed by the zirconium phosphate layer in the sorbent cartridge.

The pump can be any suitable type of pump including, for example, a reversible pump such as a peristaltic pump. The pump may alternatively be a membrane pump which includes a first valve located on a first side of the membrane pump and a second valve located on a second side of the membrane pump. In such a configuration, the control unit is programmed to switch states of the first and second valves in conjunction with the operation of the membrane pump in order to move the fluid (such as a spent dialysis fluid) from the patient or dialyzer through the sorbent cartridge to the storage container and back to the patient or dialyzer.

The system may include one or more valves between the storage container and the patient or dialyzer. The control unit can thus be further programmed to operate the one or more valves and the pump to move the fluid (such as a spent dialysis fluid) from the patient or dialyzer through the sorbent cartridge to the storage container and back to the patient or dialyzer.

An infusion solution can be in fluid communication with the patient or dialyzer. Prior to entering the patient or dialyzer, the infusion solution can be used to replenish the cleaned dialysis fluid with the necessary electrolytes (e.g., calcium, magnesium, etc.) glucose and modify the pH of the dialysis fluid prior before being transferred back to the patient or dialyzer. The control unit can be programmed to cause the infusion solution to be metered into the dialysis fluid while the dialysis fluid is caused to flow in the second direction. The dialysis system can include a second pump, controlled by the control unit, for metering the infusion solution.

The dialysis system can include a heater such as an inline heater or a batch heater operable with the storage container.

The control system can include sensors (pH, electrolyte, conductivity, glucose, temperature etc.) to monitor the physical/chemical properties of the dialysis fluid leaving and entering the patient. The control system can further include the necessary battery/power components, controls, and processors to control the different components of the dialysis system in order to operate the dialysis system as described above.

In another general embodiment, the present disclosure provides a system for dialysis, hemofiltration and/or hemodiafiltration. The system can be used for any suitable dialysis therapy including peritoneal dialysis, hemodialysis, hemofiltration, hemodiafiltration, etc. The system comprises a sorbent cartridge in fluid communication with at least one of a patient or a dialyzer. The sorbent cartridge comprises a housing including a urease later followed by a zirconium phosphate layer. In other configurations, the sorbent cartridge includes a urease layer followed by a zirconium phosphate layer, followed by at least one of a second zirconium phosphate layer, a zirconium oxide layer and a carbon layer. In still other configurations, the sorbent cartridge does not include a second zirconium phosphate layer. The system also comprises a storage container and an infusion solution in fluid communication with the sorbent cartridge and the patient or dialyzer. A pump can be used to move a fluid such as a spent dialysis fluid from the patient or dialyzer through the sorbent cartridge to the storage container and back to the patient or dialyzer.

A control system is in communication with the sorbent cartridge, the storage container, the infusion solution, and the pump. The control system is configured to recirculate a spent dialysis fluid into the sorbent cartridge in a first direction wherein the urease layer is first contacted by the dialysis fluid before the zirconium phosphate layer for at least two or more cycles followed by storing of the dialysis fluid in the storage container. A cycle refers to a specific volume of water that passes through the sorbent cartridge at least once.

The number of cycles will be determined by the level of ammonium in the dialysis fluid. There should be a sufficient number of cycles so that the ammonium level is below a threshold level for patient safety (e.g., 20 ppm). After the dialysis fluid is below the threshold level, the cleansed dialysis fluid can be stored in the storage container for a desired amount of time.

After the desired time, the dialysis fluid from the storage container can then be transferred back to the patient or the dialyzer. Prior to entering the patient or dialyzer, the infusion solution can be used to replenish the cleaned dialysis fluid with the necessary electrolytes (e.g., calcium, magnesium, etc.) glucose and modify the pH of the dialysis fluid before being transferred back to the patient or dialyzer.

The control system can include sensors (pH, electrolyte, conductivity, glucose, temperature etc.) to monitor the physical/chemical properties of the dialysis fluid leaving and entering the patient. The control system can further include the necessary battery/power components, controls, and processors to control the different components of the dialysis system in order to operate the dialysis system as described above.

Additional features and advantages are described herein, and will be apparent from, the following Detailed Description and the figures.

DETAILED DESCRIPTION

The present disclosure relates to methods of providing dialysis treatment. Additionally, the present disclosure relates to systems for providing dialysis. More specifically, in an embodiment, the present disclosure provides improved cartridges that are used to remove uremic toxins.

In a preferred embodiment, the present disclosure relates to systems and components for use in continuous flow peritoneal dialysis procedure. However, it should be noted that the present disclosure can be used in a variety of methods for providing dialysis including hemodialysis and peritoneal dialysis Continuous flow peritoneal dialysis is achieved by continuously infusing into and draining from the peritoneum a solution. For example, a closed loop or recirculating dialysis can be used where the solution is continuously recirculated to the patient. This can have the advantage of substantially reducing the amount of solution needed for a treatment. However, it is necessary to regenerate the solution with the exact glucose and electrolyte requirements required by the patient. This therapy is designed to be performed primarily at night.

Figure 1:
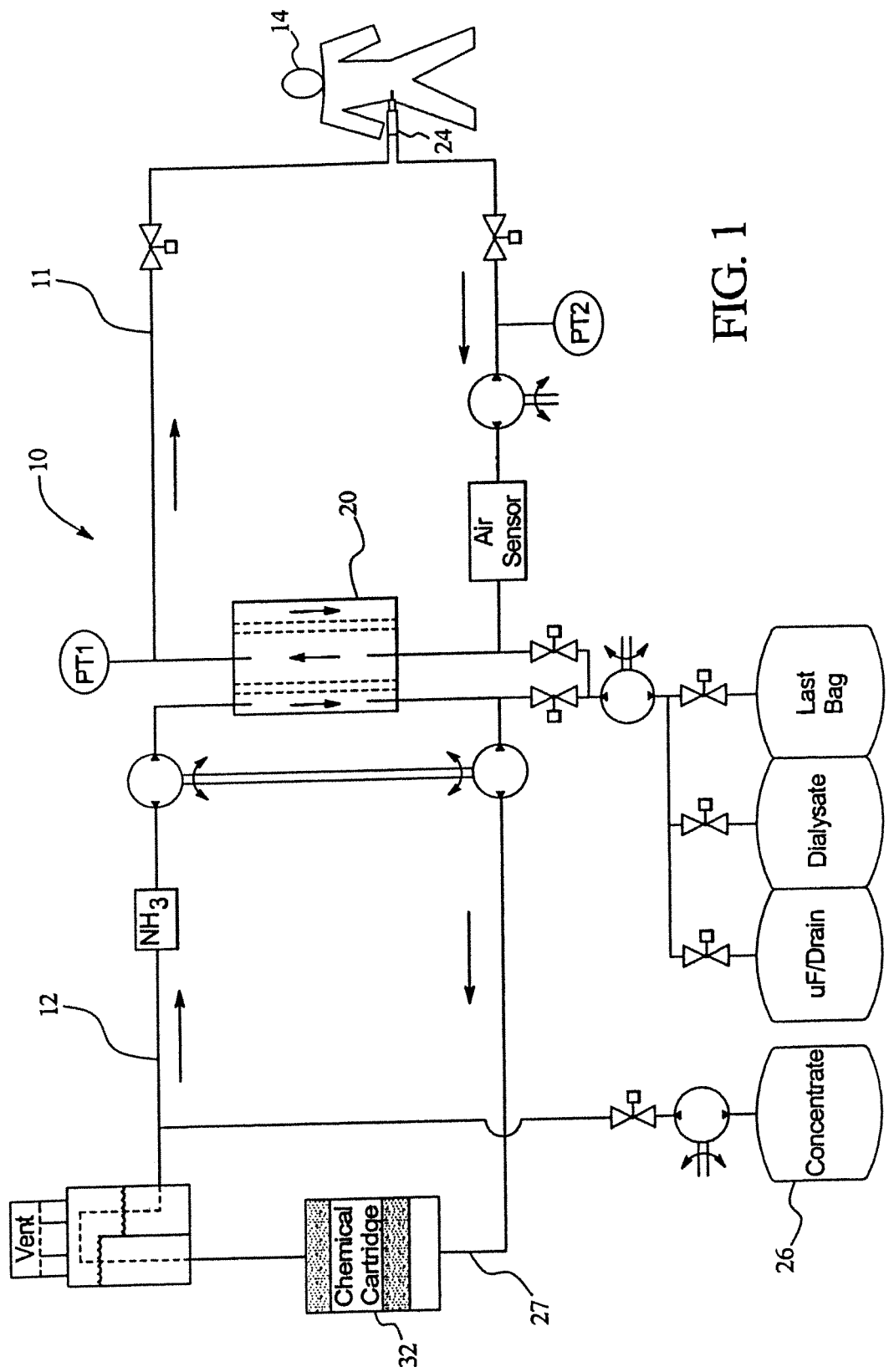
FIG. 1 illustrates schematically a system for performing dialysis pursuant to the present disclosure.

Generally, the system comprises a disposable set including a pump cassette, cartridge, dialyzer, and solution concentrate. FIG. 1 illustrates generally a schematic of the system 10 for providing dialysis treatment pursuant to the present disclosure.

As illustrated in FIG. 1, two loops are provided: a patient loop 11; and a regeneration loop 12. However, it should be noted that the present disclosure can be used in a system including only one loop or more than two loops. The patient loop 11 is used to dialyze the patient 14 with dialysate. The regeneration loop 12 is used to regenerate the dialysate. As illustrated generally, the dialysate is pumped from a bag 16 in the patient loop 11 into the patient 14 through a catheter 24. Spent fluid is then fed from the patient 14 back into the dialyzer 20.

A variety of components can be used in the patient loop. In a preferred embodiment a dual lumen catheter 24 is used. The dual lumen catheter provides for continuous, flow in to and out of the peritoneal cavity of the patient. To this end, the dual lumen catheter is implanted in the patient. An example of a catheter for use in the system 10 of the present disclosure is disclosed in U.S. patent application Ser. No. 09/689,508, filed on Oct. 12, 2000, and entitled "Peritoneal Dialysis Catheter," the disclosure of which is incorporated herein by reference. However, it should be noted that two single lumen catheters can be used as well as a single lumen catheter.

To regenerate the dialysate, the regeneration loop 12 is provided. In the embodiment illustrated, the regeneration loop 12 preferably includes concentrate in a container 26, a cartridge 32, an ultrafiltrate (UF) pump, and a UF collection means that communicates with the patient loop 11 via the dialyzer 20. A concentrate pump is provided to pump the concentrate 26 from the container through fluid path 27. The fluid in the regeneration loop is pumped through the dialyzer 20 in a counter current fashion to the fluid in the patient loop 11.

The dialyzer 20 is provided to remove water and small solutes such as urea, and creatinine from spent dialysate in the patient loop 11. The dialyzer 20 provides a sterile independent barrier between the patient loop 11 and the regeneration loop 12. Any dialyzer 20 can be used that provides a high clearance of small molecules across the dialyzer. Uric acid will diffuse across the dialyzer, ultrafiltrate is also removed.

It should be noted that although the cartridge 32 of the present disclosure is illustrated as being used in a two loop system, it can be used in other systems. For example, it is envisioned that the cartridge can be used in a one loop system.

Figure 2:
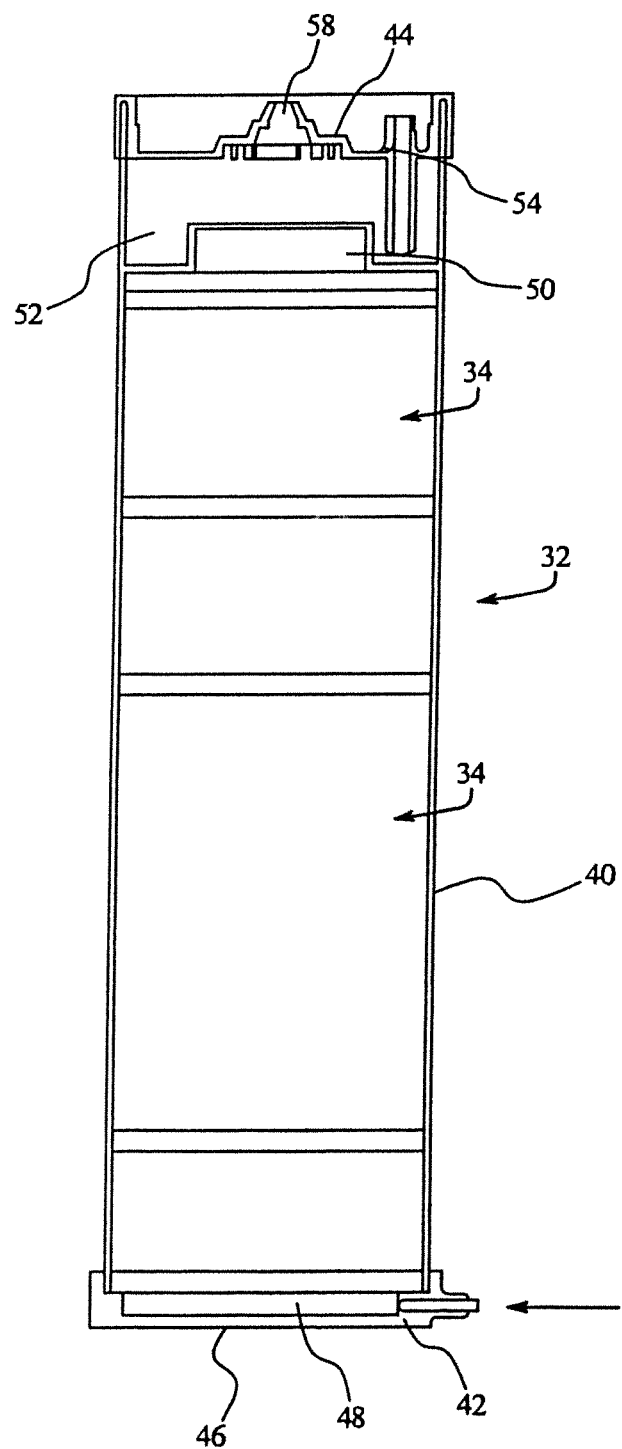
FIG. 2 illustrates a cross-sectional view of an embodiment of the cartridge of the present disclosure.

Referring now to FIG. 2, a cross-sectional view of an embodiment of the cartridge 32 of the present disclosure is illustrated. The cartridge 32 includes a resin bed 34 that is designed to modify the chemistry of the recirculating dialysate and remove uremic toxins. At the same time, pursuant to the present disclosure, the cartridge 32 maintains electrolyte concentrations and the solution pH of the dialysate at physiologic levels.

The cartridge 32 generally comprises: a main body 40, an inlet cap 42, the resin bed 34, and an outlet cap 44. In the embodiment illustrated, fluid is routed into the cartridge 32 through the inlet cap 42 that is located at a bottom 46 of the cartridge 32. In the embodiment illustrated, a small open header chamber 48 prior to the resin bed 34 is used to distribute the flow of fluid evenly across the cross-section of the cartridge 32 and thereby the resin bed 34. The fluid preferably flows upwardly through the resin bed 34.

In the embodiment illustrated, downstream of the final section of the resin bed 34 there is located another open header chamber 50. The second open header chamber 50 is located before a gas separation chamber 52. The second header chamber 50 is used to maintain an even fluid velocity distribution throughout the resin bed 34.

The liquid level in the gas separation chamber 52 is maintained within a specified range to provide an air space above the liquid in the cartridge 32. Gases that are produced during therapy, e.g., carbon dioxide, are vented from the cartridge 32 to the environment through a passage 54 on the outlet cap 44. If desired, this passage 54 may include a filter member. A submerged, or partially submerged, barrier in the gas separation chamber 52 produces a flow pattern that restricts gases from being drawn to the liquid outlet.

At the outlet cap 44 of the cartridge 32 the liquid outlet port 58 is located. The liquid outlet 58 port removes liquid from the chamber of the cartridge 32 through the outlet cap 44 using a siphon action. If desired, an additional port may be used to add a chemical concentrate to the volume of liquid in the gas separation chamber to reconstitute the chemical composition of the fluid outflow.

In an embodiment, the interior of the cartridge 32 has a rough surface. The rough surface is designed so that it prevents fluid from flowing along the sides of the exterior by passing the resin bed 34.

The resin bed 34, in part, functions to remove waste. In this regard, generally waste is removed using a two-step process. The steps consist of an enzymatic conversion of urea using urease followed by subsequent removal of the conversion byproducts. In the enzymatic reaction, one mole of urea is decomposed into two moles of ammonia and one mole of carbon dioxide. Ammonia ($NH_3$) is primarily (>95%) present as ammonium ion ($NH_4^+$), since its pKa of 9.3 is substantially greater than the solution pH. The carbon dioxide that is formed can either be present as dissolved carbon dioxide or as bicarbonate ion, depending on the solution pH. Since the pKa for this equilibrium is 6.1, both species may be present in substantial quantities under conditions of use. In addition, if the solution is in communication with a gas phase, the dissolved carbon dioxide is in equilibrium with the carbon dioxide present in the gas phase.

The resin bed includes at least four layers, although more layers can be used. Generally, the layers of the resin bed comprise at least: a urease layer; a layer of zirconium phosphate; a layer of zirconium oxide; and a layer of carbon.

The purpose of the urease layer is to enzymatically convert urea that is present in the solution that is flowing through the resin bed 34 to ammonia and carbon dioxide. In solution, ammonia acts as a base since the formation of ammonium results from the donation of $H^+$. Similarly carbon dioxide ($CO_2$) acts as an acid, since the formation of bicarbonate ($HCO_3$) donates H+ to solution. The net result of the urease reaction is to increase the pH.

In an embodiment, 25 to 250 mg of urease are used, although any amount of urease can be used that is sufficient to convert the urea present in the solution to ammonia and carbon dioxide. Preferably, urease comprises the first or second layer of the resin bed.

A variety of urease materials can be used. For example, crosslinked enzyme crystals of urease (Urease-CLEC) can be used. This material is ultra pure and has high specific activity. Therefore, a very small quantity of this urease is sufficient to provide the desired urea-conversions.

By way of example, the amount of urease-CLEC required was optimized for two different internal diameters of the cartridge, 3¼" and 1¼" respectively. Next, in order to determine the optimal contact time between urease-CLEC and the substrate stream, the enzyme was blended with powdered Zirconium Oxide (ZO). Table 1 shows the optimized amount of urease-CLEC and ZO required to obtain a urea conversion >90%. The quantity of enzyme used was stable to sterilization with 40 kGy γ-radiation. The flow rate used in all above experiments was 100 ml/min.

TABLE 1

Summary of urease-CLEC required for urea conversion

| Column Diameter (inch) | Amount of urease-CLEC required (mg) | Amount of ZO required (gm) | γ-sterilization dose (kGy) | % Urea Conversion |
|---|---|---|---|---|
| 1.25 | 50 | 25 | >40 | 90 |
| 3.25 | 150 | 150 | >40 | 97 |

For this particular approach of using urease-CLEC, the primary challenge is in the development of procedures for blending very small quantities of urease-CLEC with large quantities of ZO. Where as, the small quantity is advantageous for easy containment within the polymer matrix of an ultrafiltration membrane. The use of these urease-impregnated ultrafiltration membranes provide several benefits over the currently available methods:

1) Better urease containment.
2) Reduced cartridge size resulting in enhanced ease of use by patient.
3) Ease of use during cartridge manufacture
4) Increased safety over the existing system (due to better containment of urease in the cartridge)

Table 2 shows the urea conversion observed at various flow rates using a urease-CLEC impregnated membrane. The membrane tested had a diameter of 1 inch, thus, the flow rates used were 1.3, 2.7 and 5.3 ml/min, which correspond to a flux of 50, 100 and 200 ml/min through a 3.25 inch membrane.

TABLE 2

Sample results obtained from a γ-sterilized urease-CLEC-impregnated membrane

| Amount of Urease-CLEC (mg) | Membrane diameter (inch) | Flow rate (ml/min) | γ-sterilization dose (kGy) | % Urea Conversion |
|---|---|---|---|---|
| 15.85 | 1 | 1.3 | 40 | 87.3 |
| 15.85 | 1 | 2.7 | 40 | 79.2 |
| 15.85 | 1 | 5.3 | 40 | 66.9 |

Although, the urea conversions observed are lower than required, better conversions can be expected from membranes prepared with larger quantities of urease-CLEC. Additionally by employing two membranes in each cartridge a higher overall urea conversion can be obtained.

By way of further example, alumina-stabilized urease can also be used. Upon wetting, the urease dissolves but, it is immediately absorbed by the alumina particles that are located in close proximity. The end result is urease that is physically absorbed by the alumina in close proximity. This urease exposed to γ-irradiation at a dose of 15 kGy in the presence of γ-irradiation retained 75% of its initial activity.

Referring now to the zirconium phosphate layer, zirconium phosphate can absorb, under certain conditions, ammonium ion, calcium, magnesium, and sodium. Ammonium ion is removed from solution via an ion exchange process using zirconium phosphate. Zirconium phosphate contains two counter-ions—hydrogen ($H^+$) and sodium ($Na^+$). Release of the counter-ions is determined by the solution pH and the current loading state of the resin. In addition to its role as an ion exchange resin, zirconium phosphate also has a considerable buffering capacity.

If the loading state pH of the resin is 6.2 then when in contact with an (acidic) solution having a pH of less than 6.2, the resin will release $Na^+$ in exchange for $H^+$, even in the absence of any other ions. In contact with a (basic) solution having a pH of greater than 6.2, the resin will release $H^+$ in exchange for $Na^+$, even in the presence of other cations. In contact with a solution having a pH of 6.2 and containing ammonium, the resin will exchange a mixture of $Na^+$ and $H^+$ ions for $NH_4^+$ such that its equilibrated pH remains unchanged. The zirconium phosphate resin possesses excellent capacity for ammonium, and this capacity is unaffected by changes in equilibrated pH within a given range (pH 6.0-7.2).

The desired pH of the zirconium phosphate will depend, in part, on its location in the resin bed, e.g., the component it is designed to remove. To this end, the zirconium phosphate layer can have a pH of between approximately 2 to about 8. Preferably, zirconium phosphate is present in a range of approximately 200 to about 800 grams. The amount of zirconium phosphate necessary is at a minimum that amount that is sufficient to remove the ammonium that is generated. The level of ammonium generated is determined by the urea that is to be removed by the cartridge. Thus, the amount of zirconium phosphate equals the ammonium to be removed divided by the capacity of the zirconium phosphate, to remove ammonium, which can be determined experimentally.

Figure 3:
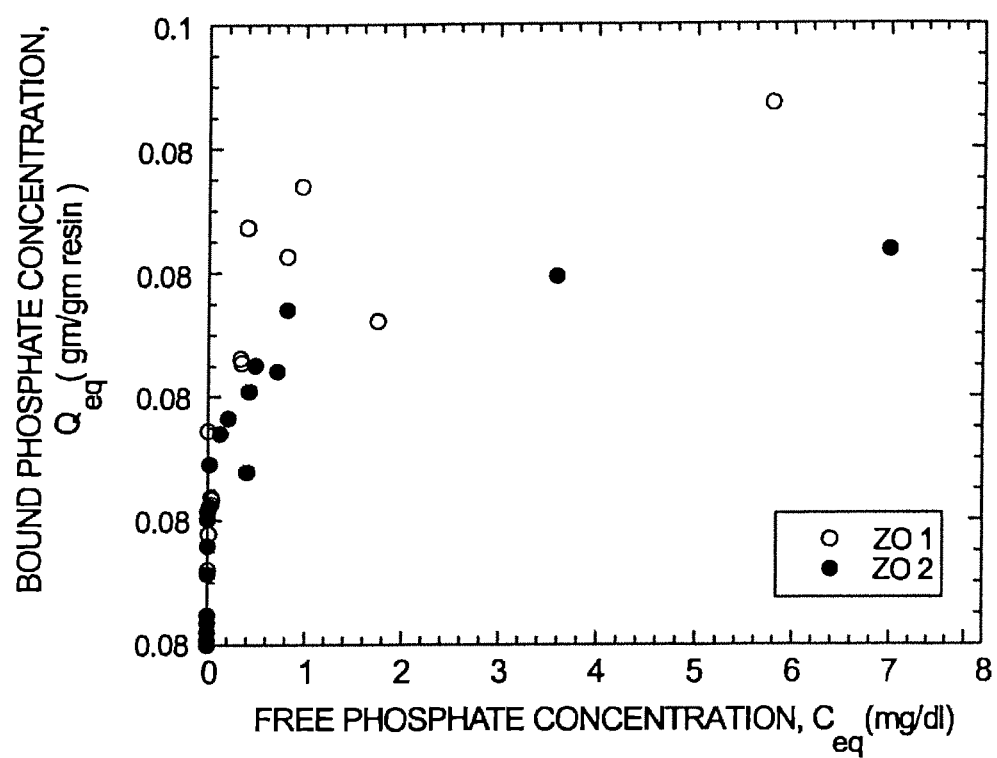
FIG. 3 illustrates graphically ammonium effluent concentration (ppm) versus mass ammonium delivered (mEq) for zirconium phosphate available from two suppliers (Sorb technologies and magnesium elektron).

For example, a process for determining the quantity of zirconium phosphate required in the device can be determined as follows. Equilibrium data is employed to make a first pass guess at the amount of zirconium phosphate required. For a given cartridge containing a particular amount of zirconium phosphate, the effluent ammonium concentration profile is obtained. The capacity of a given cartridge is defined as the mass of ammonium delivered at the time that the effluent concentration exceeds a prescribed level. In an embodiment, this effluent cutoff level is set at 20 ppm. For example, in the data from FIG. 3, for a small prototype device, the ammonium capacity is approximately 4.2 mEq for 10.5 g zirconium phosphate, an input concentration of 3.9 mEq/L ammonium, and a bulk flow rate of 8.3 mL/min (breakthrough at the 20 ppm level occurs after absorption of 4.2 mEq ammonium).

In an embodiment, it is believed that the quantity of zirconium phosphate required is on the order of approximately 600 to about 800 g. In an embodiment, zirconium phosphate will comprise more than half of the cartridge by weight. As to its location in the resin bed, preferably zirconium phosphate can comprise the first layer through all but the last layer of the resin bed (not including the carbon layer). Moreover, multiple zirconium phosphate layers can be used.

Referring now to the zirconium oxide layer, zirconium oxide resin is an amphoteric resin. This means that the resin's ion exchange properties are dependent on the solution pH. If the solution pH is much lower than the pI of the resin, the resin acts as an anion exchange resin. If the solution pH is much greater than the pH of the resin, the resin acts as a cation exchange resin. If the solution pH is near its pI, the resin demonstrates properties of a mixed bed, exchanging both cations and anions. This latter behavior of a mixed bed occurs throughout the physiologic pH range.

The zirconium oxide layer removes phosphates. The zirconium oxide layer, depending on the pH, can also function to remove sodium. Preferably the zirconium oxide layer has a pH of approximately 6 to about 13.

Figure 4:
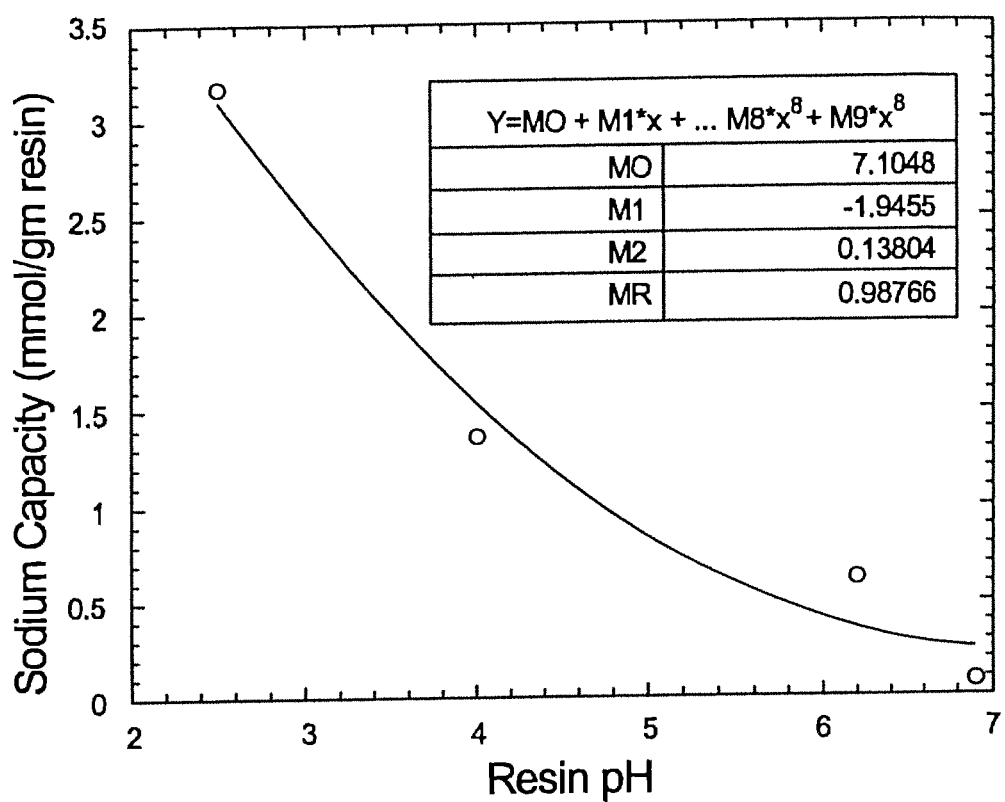
FIG. 4 illustrates graphically sodium capacity as a function of zirconium oxide pH.

The phosphate capacity of the resin is very high, thus, the size of the layer is governed by how much sodium needs to be removed. In like fashion, the amount of zirconium oxide is thereby determined by the capacity of the zirconium oxide that is used to remove sodium. FIG. 4 illustrates graphically the sodium capacity of zirconium oxide as a function of its pH.

The zirconium oxide layer functions to remove any phosphate that may not have been absorbed by the other components of the resin bed. Further, the zirconium oxide layer controls the pH of the solution leaving the cartridge. Accordingly, preferably the zirconium oxide layer, if it is the last layer (not including the carbon layer) of the cartridge 32, has a pH of approximately 7 to about 9 and in a preferred embodiment, approximately 7.4. Although preferably the zirconium oxide layer is the last layer (not including the carbon layer), multiple zirconium oxide layers can be used.

In an embodiment, zirconium oxide is utilized that has been modified by removing the nitrate ion as the counter ion. In this regard, the nitrate ion was exchanged with bicarbonate ion by treating the zirconium oxide with 15% sodium carbonate solution to a pH of approximately 11.3. The mixture was then washed extensively with water to remove residue sodium nitrate and sodium carbonate. The resin was then dried under high vacuum at an RT of approximately 24 hours. The resulting resin (0.5 g/mL in water) at a pH of approximately 8.5, and a conductivity of 155.1 us/cm. The dried resin was further modified by suspending the resin in water and adding hydrochloric acid until a pH of 7 was achieved. Following the pH adjustment, the resin was washed to remove residual chloride and sodium ions. After each of the washing steps the resin filtrate pH and conductivity was measured. After wash 1, the paper pH was 6.5 to 7 and conductivity 464 us/cm; after wash 2, paper pH 6.5 to 7 and conductivity 186.5 us/cm; and wash 3 pH (paper) 6.5 to 7, conductivity 38.2 us/cm. It should be noted that washes 1 and 2 were performed by letting the mixture settle and then decanting the supernatant to waste. After wash 3, the solid was collected via vacuum filtration through a 0.2 micron pore size nylon filter. The solid was dried via vacuum on the filter apparatus between 6 to 12 hours to yield the final product.

Referring now to the carbon layer, carbon removes creatinine, uric acid or other organic molecules that still may be present in the solution. For example, the carbon layer removes creatinine. The amount of creatinine that needs to be removed by this cartridge is approximately 0.5 g to about 3.0 g. Although the volume of carbon can comprise a wide range, preferably approximately 50 to about 200 grams of carbon is used. Preferably, the carbon will be of the type that has the ability to remove less than 30 grams of glucose from the peritoneal dialysis solution. Thus, such a carbon layer will not remove an excess amount of glucose from the dialysis solution. Activated carbon sold under the designation LP-50 by Carbochem, Ardmore, Pa., has been found to function satisfactorily in this regard. Other carbons can be used. It is believed that carbons that are coconut shell based having a particle size of 20×50 will also work. It should be noted that the carbon layer can be located as any of the layers in the resin bed, although in a preferred embodiment it is the last layer.

Figure 5:
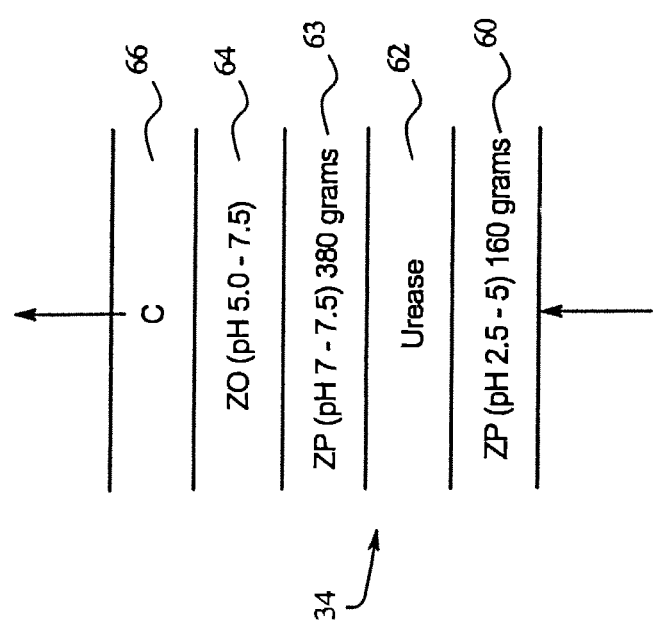
FIG. 5 illustrates an embodiment of a cross-sectional view of a resin bed of a cartridge of the present disclosure.

FIG. 5 illustrates an embodiment of the resin bed 34 of the present disclosure. The resin bed 34, in the illustrated embodiment includes five layers 60, 62, 63, 64, and 66. The first layer 60 is a zirconium phosphate layer having a pH of approximately 2.5 to about 5 and comprising approximately 160 grams. The second layer 62 is a layer of urease comprising approximately 25-250 mg of urease-CLEC in 25 gm zirconium phosphate/zirconium oxide or 50-100 gm of urease which is not crosslinked from other sources. The third layer 63 comprises zirconium phosphate having a pH of approximately 7 to about 7.5; preferably there are approximately 380 grams of zirconium phosphate. The fourth layer 64 is approximately 50 to about 75 grams of zirconium oxide at a pH of approximately 5 to about 7.5. The last layer 66 comprises approximately 50 to about 200 grams of carbon and in an embodiment, 130 grams.

In the resin bed 34 the first layer 60 is used to remove sodium, Ca, and Mg. Also this layer 60 will adjust the pH of the solution facilitating the conversion of urea to ammonium by the urease, second layer 62. The third layer 63 removes the ammonium generated by the urease layer 62. To this end, the zirconium phosphate needs to have a pH of greater than or equal to 5; in the illustrated embodiment the pH is 7 to 7.5. The fourth layer 64 of zirconium oxide removes the phosphate and adjusts the pH to approximately 7.4. The size of the fourth layer 64 needs to be such so as to allow the pH of the solution that exists the resin bed 34 to be adjusted to the desired pH. The last layer 66 is the carbon layer that removes any remaining impurities including creatinine.

In CFPD it is required to remove anywhere from approximately 5 to about 20 gm urea/day. Table 1 below provides the amount of resin required for the various layers in order to remove 5, 10, and 20 gm of urea.

For example, removal of 10 gm of urea generates 342 mmol of ammonia and 171 mmol of bicarbonate. Using the resin bed of FIG. 4 to remove 342 mmol of ammonia, a 380 gm layer of zirconium phosphate (resin pH=6.2, ammonia capacity=0.9 mmol/gm resin) was found to be necessary. In the process of removing the 342 mmol of ammonia the resin will release 342 mmol of sodium into the solution. Zirconium phosphate at pH of 6.2 has a capacity of 0.63 mmol/gm resin for sodium and hence will re-adsorb 342-127 mmol of sodium. As a result, an additional 127 mmol of sodium needs to be removed from the solution after passing through layer 63. Layer 60, which is also made up of zirconium phosphate removes this amount of sodium. The amount of zirconium phosphate required to remove this amount of sodium varies as a function of pH of the resin. Table 3 shows the amount of zirconium phosphate at various pHs required to remove 127 mmol of sodium. The amount of zirconium phosphate at various pHs required to remove sodium is equal to:

sodium capacity (mmol/gm resin)=7.1-1.945 (pH of ZP) and 0.138 (pH of Zp)$^2$.

Accordingly, at a pH of 2.5, the sodium capacity is 3.1 mmol/gm ZP. From Table 3, at a pH of 7.2, to remove 171 mmol of sodium we need 53.4 gm of zirconium phosphate.

The size of the zirconium oxide layer is controlled by the amount required to raise the pH from 6.2 to neutral during the entire therapy time. This amount is easily obtained from the pH profile curve. A gram of zirconium oxide resin has the capacity to raise the pH of approximately 0.45 L of solution from 6.2 to neutral. In an embodiment of a dialysis method it is necessary to process 48 L of the solution in 8 hr, resulting in a requirement of 106 gm of resin. The amount of zirconium oxide resin required to remove all of the phosphate in the solution was found to be in the range of 60-80 gm. Thus the 106 gm of zirconium oxide required to adjust the pH will also meet the requirement for the removal of phosphate.

TABLE 3

Amount of Resin for 5, 10, 20 gm Urea Removed

| ZP Layer 3 PH | Ammonia to be removed mmol | ZP Layer 3 size (gm) | Sodium to be removed (mmol) | ZP layer size at various pHs (gm) | | | ZO Layer 4 size(gm) |
|---|---|---|---|---|---|---|---|
| | | | | 2.5 | 4.0 | 5.0 | |
| 7.2 | 171 | 285 | 171 | 53.4 | 114 | 190 | 60-80 |
| 6.2 | 171 | 285 | — | — | — | — | 80-100 |
| 7.2 | 342 | 380 | 342 | 107 | 228 | 380 | 60-80 |
| 6.2 | 342 | 380 | 127 | 40 | 85 | 141 | 106 |
| 7.2 | 684 | 456 | 684 | 213 | 456 | 760 | 80-100 |
| 6.2 | 684 | 456 | 396.7 | 124 | 264 | 441 | 130 |

Figure 6:
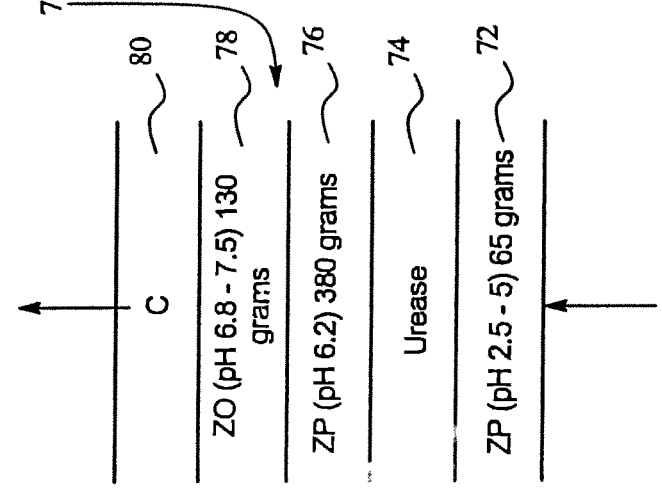
FIG. 6 illustrates a further embodiment of a resin bed of a cartridge of the present disclosure.

Referring now to FIG. 6 another embodiment of the resin bed of the present disclosure is illustrated. The resin bed 70 includes a five layer structure. The layers are similar to the resin bed 34 of FIG. 4. In this regard, the first layer 72 is zirconium phosphate, the second layer 74 is urease, the third layer 76 is zirconium phosphate, the fourth layer 78 is zirconium oxide, and the fifth layer 80 is carbon.

However, the first 72, third 76, and fourth 78 layers are slightly different than their counterparts in FIG. 4. In this regard, the first layer 72 of zirconium phosphate preferably comprises 65 grams having a pH of approximately 2.5 to about 5. The third layer of zirconium phosphate has a pH of greater than 5 and in a preferred embodiment 6.2. This layer also comprises, as in the embodiment of FIG. 4, 380 grams. The fourth layer of zirconium oxide comprises approximately 130 grams and has a pH of approximately 6.8 to about 7.5.

In the resin bed 70, once again, the first layer 72 removes the sodium but does not remove the ammonium. The first layer 72 will also adjust the pH of the solution for converting urea to ammonium by the urease layer. The pH of the solution coming out of the first layer 72 will be approximately the pH of the resin. The lower the pH of the resin, the more sodium is removed. As the solution exits the urease layer 74 and enters the third layer 76 of zirconium phosphate, the ammonium is removed. As the pH of the zirconium phosphate is increased, more ammonium is removed. A pH of at least 5 is required in order to remove the ammonium. Once again, the fourth layer 74 of zirconium oxide removes the phosphate and adjusts the pH to 7.4. The last layer 80, the carbon layer, once again removes any remaining impurities.

Figure 7:
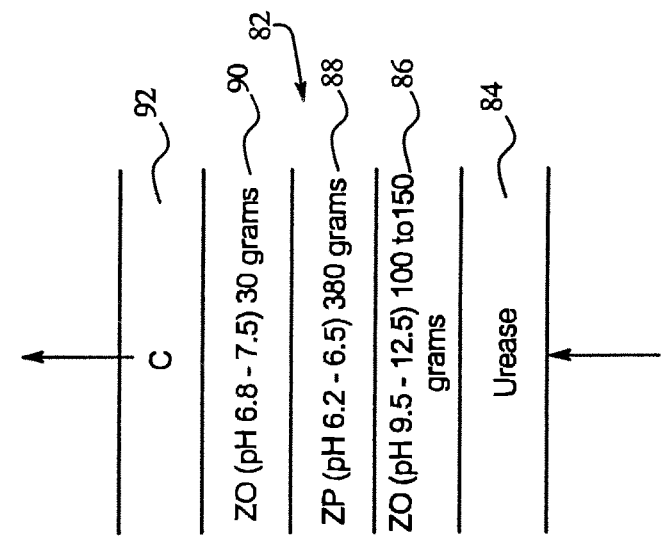
FIG. 7 illustrates a still further embodiment of a resin bed of a cartridge of the present disclosure.

Referring now to FIG. 7, a further embodiment of a resin bed 82 is illustrated. In this embodiment, the first layer 84 comprises urease. The second layer 86, in an embodiment, comprises zirconium oxide at a pH of approximately 9.5 to about 12.5. Preferably 100 to 150 grams of zirconium oxide are present. The third layer 88 comprises zirconium phosphate at a pH of approximately 6.2 to about 6.5. Approximately 680 grams are present. The fourth layer 90 comprises zirconium oxide at a pH of approximately 6.8 to about 7.5 with preferably approximately 30 grams being present. The last layer 92 comprises carbon.

In the resin bed 82 the zirconium oxide layer 86 functions in the role of zirconium phosphate in the other resin beds (34 and 70). To this end, it removes the sodium. The amount of sodium removed is based on the capacity of the zirconium oxide to remove sodium. The zirconium oxide functions to remove sodium due to its high pH. On the other hand, one of the disadvantages of this structure as compared to the other resin beds (30 and 70) is that a high pH is required so that as the solution exits the second layer 86 it is at a higher pH.

Generally, it should be noted that preferably the resin beds of the present disclosure are structured so that urea is removed in either the first or second layers. Then preferably sodium is removed. After the sodium is removed, ammonium and then phosphate is removed. Additionally, the zirconium oxide layer functions to control the pH of the solution exiting the resin bed.

As previously noted, the resin bed of the cartridge can comprise any number of layers greater than four. It should also be noted that the layers may not have discrete boundaries, but, may be blended together. For example, it is possible to have a gradient of two materials between the zirconium oxide and the zirconium phosphate layers.

By way of example, and not limitation, real-time values for solute concentration at the inlet and outlet of cartridge 32 of the present disclosure will now be set forth. Due to mixing and mass transfer effects, these concentrations will be different at other locations of the system.

| Parameter | Input value | Output value |
| --- | --- | --- |
| Urea Nitrogen Concentration [mg/dL] | 2-24 | <10% of input value |
| Creatinine concentration [mg/dL] | 0.5-3.0 | <20% of input value |
| Phosphate concentration [mg/dL] | 0.45-3.0 | <20% of input value |
| Sodium concentration [mEq/L] | 122-142 | 122-142 |
| Calcium concentration [mEq/L] | 2.5 | <0.2 |
| Magnesium concentration [mEq/L] | 0.5 | <0.05 |
| Ammonium concentration [ppm] | n.a. | <20 |
| Aluminum concentration [ppb] | n.a. | <10 |

Average Values

Preferably, the time-averaged concentration of the following parameters will be maintained within the given boundaries as measured in the cartridge effluent:

| | |
| --- | --- |
| pH | 7.0-7.4 |
| Sodium [mEq/L] | 127-137 |
| Chloride [mEq/L] | 85-98 |
| Bicarbonate [mEq/L] | 25-35 |

The pH of the effluent from the cartridge will be maintained between 6.5 and 8.0 at all times Net Solute Removal/Addition

| Parameter | Amount Removed |
| --- | --- |
| Urea-nitrogen | 9.8 at an input concentration of 20 mg/dL |
| Creatinine | 1.44 g |
| Phosphate | 1.44 g |
| Sodium | 20-60 mEq |
| Bicarbonate | 20-60 mEq |

Note: The capacity to process urea, creatinine, or phosphate depends upon the input concentration of that component. The capacity for a given component is defined by the component breakthrough, which is the amount absorbed by the cartridge when the effluent concentration exceeds a prescribed level (i.e., 10% of the input value). For safety reasons, Ammonium breakthrough levels are defined in absolute terms at 20 ppm.

As noted above, a variety of different layer structures for the resin bed are possible within the cartridge 32. In constructing the cartridge 32, the processes occurring in the cartridge must be considered. While the cartridge performs its primary task of removing urea, creatinine, phosphate, and other toxins, the by-products of this process result in changes in dialysate composition in three important respects: 1) sodium; 2) pH; and 3) bicarbonate. These three parameters are intimately related.

Sodium can be affected by three distinct processes within the cartridge:

1) Release of sodium in exchange for ammonium and other cations (calcium, magnesium, potassium). The maximum quantity of these cations to be absorbed will be about 650 mmol, consisting of about 430 mmol of ammonium and about 200 mmol of the other cations. The amount of sodium released during this exchange process is dependent on the equilibrated pH of the zirconium phosphate, the solution pH, and the concentration of cations in the dialysate.

2) pH equilibration of zirconium phosphate. In this process, sodium is exchanged for hydrogen ion in response to a solution pH which is different from the equilibrated pH of the resin. This exchange can occur in either direction, depending on whether the solution pH is above or below the equilibrated pH. It is expected that the solution pH will be greater than the equilibrated pH of the resin for much of the therapy, resulting in a net adsorption of $Na^+$ from solution.

3) Ion exchange of zirconium oxide. As an amphoteric resin, zirconium oxide is capable of removing sodium from solution if the equilibrium pH of the zirconium oxide is sufficiently basic.

4) Adsorption of sodium by the mixed bed (demineralization) resin, if present. The amount of sodium absorbed is entirely dependent on the quantity of mixed bed resin present.

5) Liberation of alkali upon conversion of urea. Conversion of urea is a continuous process throughout the therapy. Conversion of urea may contribute up to 430 mmol alkali, and is directly related to a patient's urea load.

6) Formation of bicarbonate during the conversion of urea. Formation of bicarbonate acidifies the solution, but this effect is partially offset by venting of carbon dioxide from solutions.

7) Venting of carbon dioxide from the cartridge loop. In solution, carbon dioxide acts as an acid. Thus, removal of carbon dioxide by its movement to the gas phase and subsequent venting out of the system results in a net loss of acid from solution.

8) Buffering of the solution by zirconium phosphate. It is expected that the solution pH will be greater than the equilibrated pH of the resin resulting in a net release of acid (W) to the solution.

9) Buffering of the solution by zirconium oxide. The zirconium oxide resin exchanges H⁺/OH⁻ if it is in contact with a solution having a pH different from its equilibrated pH.

Bicarbonate levels can be affected by three distinct processes within the cartridge:

1) Formation of bicarbonate during the conversion of urea. One mole of carbon dioxide/bicarbonate is formed from each mole of urea. Dissolved carbon dioxide is in equilibrium with bicarbonate according to the following relation:

$$pH = 6.2 + \log\frac{HCO_3^-}{CO_2(aq)}$$

Consequently, the ratio of carbon dioxide/bicarbonate formed as a result of the urease reaction is dependent on the solution pH, with more acidic conditions favoring carbon dioxide. The overall quantity of (carbon dioxide+bicarbonate) formed is dependent on the patient's urea load.

2) Venting of $CO_2$ from the cartridge loop. Dissolved carbon dioxide is in equilibrium with the partial pressure of carbon dioxide in the gas phase. Thus, carbon dioxide will bubble out of solution if the solution partial pressure exceeds the partial pressure of the gas phase.

3) Adsorption of bicarbonate by zirconium oxide. zirconium oxide resin in the hydroxyl form is capable of adsorbing bicarbonate. Conversely, zirconium oxide resin in the bicarbonate form is capable of releasing bicarbonate into the solution.

The possible manipulations within the cartridge that can be made are as follows:

1) Altering the equilibrated pH of the zirconium phosphate resin. By lowering the equilibrated pH of the resin, the amount of sodium released is reduced, the average dialysate pH is lower, and the amount of carbon dioxide formed is greater. By raising the equilibrated pH of the resin, the solution pH becomes more physiologic, but the amount of sodium and bicarbonate released is increased.

2) Altering the equilibrated pH of the zirconium oxide resin or loading the resin with various counter-ions. Hydroxyl-loaded zirconium oxide results in a more physiologic solution pH, adsorption of bicarbonate from solution and increased adsorption of cations.

By way of example and not limitation, the experiments below set forth further embodiments and analysis of the invention.

Experiment No. 1

Set forth below are tests that examined the effect of modifying the equilibrium pH of zirconium phosphate on the composition of the dialysate effluent. The primary endpoints observed were pH, sodium concentration, and bicarbonate concentration. The ideal result is an effluent pH at or near the physiologic pH of 7.4, a net sodium removal of ~50 mEq for a full-sized cartridge, and a net bicarbonate addition of ~50 mEq for a full-size cartridge. These experiments were typically conducted at a g scale of zirconium phosphate, in a manner such that the urea concentration at ammonium breakthrough is in the expected column input range during patient therapy. At this scale, appropriate performance targets are a net sodium removal of ~1 mEq and a net bicarbonate addition of ~1 mEq (or 0.5 mEq/L for a 2 liter reservoir).

The resin was modified with phosphate buffer to increase the effluent pH by the following procedure. A large reservoir of 15 mM phosphate buffer was prepared using 10.8 mM dibasic sodium phosphate, 4.2 mM of monobasic sodium phosphate and 117 mM sodium chloride. The buffer was pumped through a column of resin in single pass mode. The flow rate was scaled to achieve a residence time of ~5 minutes. The effluent pH was monitored closely, and the experiment was stopped when the effluent pH reached the desired value.

With this technique the action can be modified up to a pH of 7.2. For higher pH the same phosphate buffer is prepared and 0.1 M NaOH is added to raise the pH to the desired value.

For the modified zirconium phosphate materials, static tests were performed to determine the equilibrium capacity for ammonium. The equilibrium isotherms for the different materials are not significantly different from one another over the working concentration range [3-15 mM].

Tests were performed using a 2-liter bag as a reservoir with recirculation through columns containing the material. The bag was maintained at a uniform concentration with the aid of a shaker. The solution was pumped through the column(s) and returned to the solution bag. The bag has an outlet port with an injection site, and an inlet port that is extended 9.5 inches into the bag. The extension of the inlet port into the bag minimizes channeling between the two ports and ensures proper mixing. The solution used in these tests was Dianeal PD4 (1.5% glucose) spiked with urea and bicarbonate. Precautions were taken during the filling and sampling procedures to ensure that the integrity of the system was maintained.

All the tests were performed using a urea concentration of 10 mg/dL and a sodium bicarbonate concentration of 25 mM. The initial pH for this solution was 7.4+/−0.2. For all the tests, 10 grams of cation material were used. Two types of urease were employed in these tests, CLEC-urease from Altus Biologics (5-20 mg) and urease from Sorb Technologies (5 g mixed with 10 g alumina). For the Sorb urease a 25 mL column was used with 8 μm filters on both ends. The urease alumina mixture was sandwiched between two lays of alumina (~5 g each). The Sorbtech urease was packed dry. The CLEC-urease was packed wet, sandwiched between layers of Sephacryl (inert chromatography media from Sigma Chemicals) in a 10 ml column. No difference in performance was observed between the two forms of urease.

Prior to the experiment the urease was flushed with Dianeal to remove any labile or very small particle size enzyme. After the pump was started, time zero was defined by the appearance of fluid exiting the column outlet port. Samples were collected over time from both the inlet and outlet to the two-liter bag, and analyzed immediately for sodium, pH and bicarbonate using a blood gas analyzer (Chiron model 860, Chiba Corning).

Table 4 shows a summary of the relevant tests performed. Additional experiments were performed using a phosphate buffer.

From these tests it is apparent that the change in pH during the test is reduced when the pH of the resin is modified to a higher (than 6.2) pH. With an increase in resin pH the performance of the resin in terms of ammonia adsorption maintains the same, but more sodium is released into the system. The presence of the urease works in reducing the changes in pH.

TABLE 4

Results of small-scale test using urease and zirconium phosphate

| Resin pH | Date | Solution pH, initial | Solution pH, final | ΔpH | ΔNa$^+$ (mEq) | NH$_4^+$ bound (mEq) | ΔHCO$_3^-$ (mmol/L) |
|---|---|---|---|---|---|---|---|
| 6.2 | Apr. 21, 2000 | 7.80 | 7.13 | −0.67 | 0.5 | 7.3 | 0.5 |
| 6.8 | May 4, 2000 | 7.41 | 7.21 | −0.20 | 3.8 | 8.6 | 2.5 |
| 7.1 | Apr. 21, 2000 | 7.25 | 7.47 | +0.22 | 5.5 | 5.9 | 4.4 |
| 7.4 | May 4, 2000 | 7.45 | 7.59 | +0.14 | 5.1 | 6.5 | 2.9 |
| 7.4 | May 15, 2000 | 7.38 | 7.46 | +0.08 | 4.9 | 6.9 | 1.7 |
| 7.6 | May 6, 2000 | 7.44 | 7.47 | +0.03 | 5.5 | 8.8 | 5.3 |
| 7.6 | May 15, 2000 | 7.36 | 7.56 | +0.20 | 4.1 | 7.3 | 3.2 |

Experiment No. 2

Figure 8:
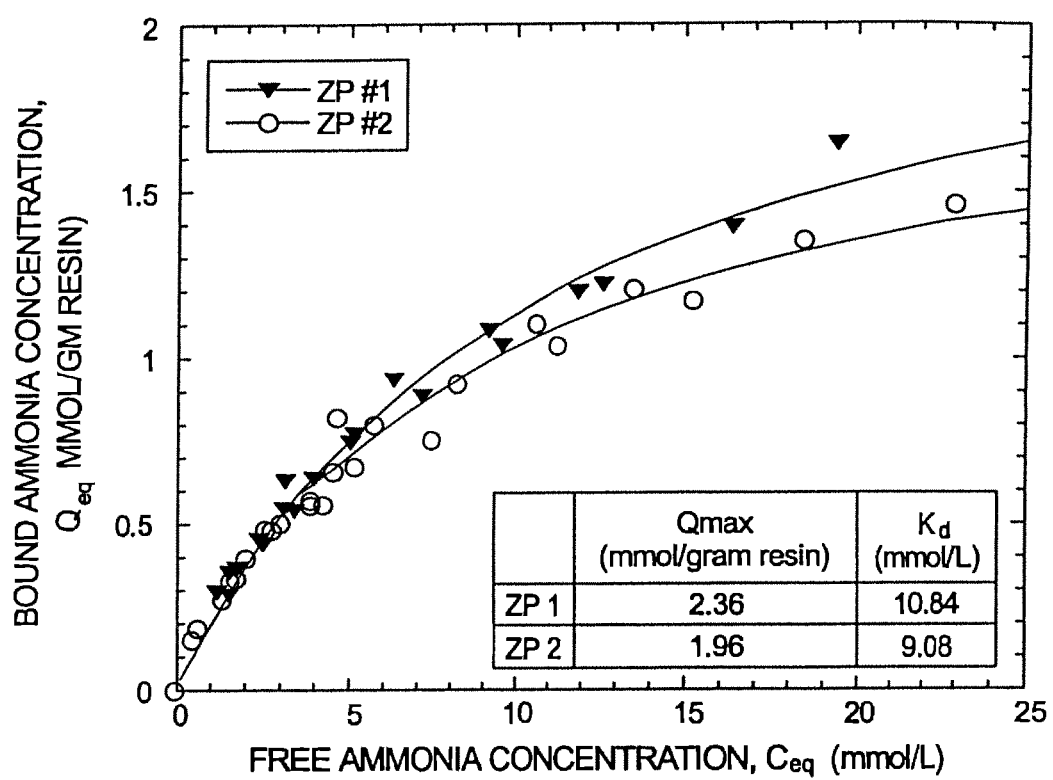
FIGS. 8-10 illustrate graphically the results of Experiment No. 2.
Figure 9:
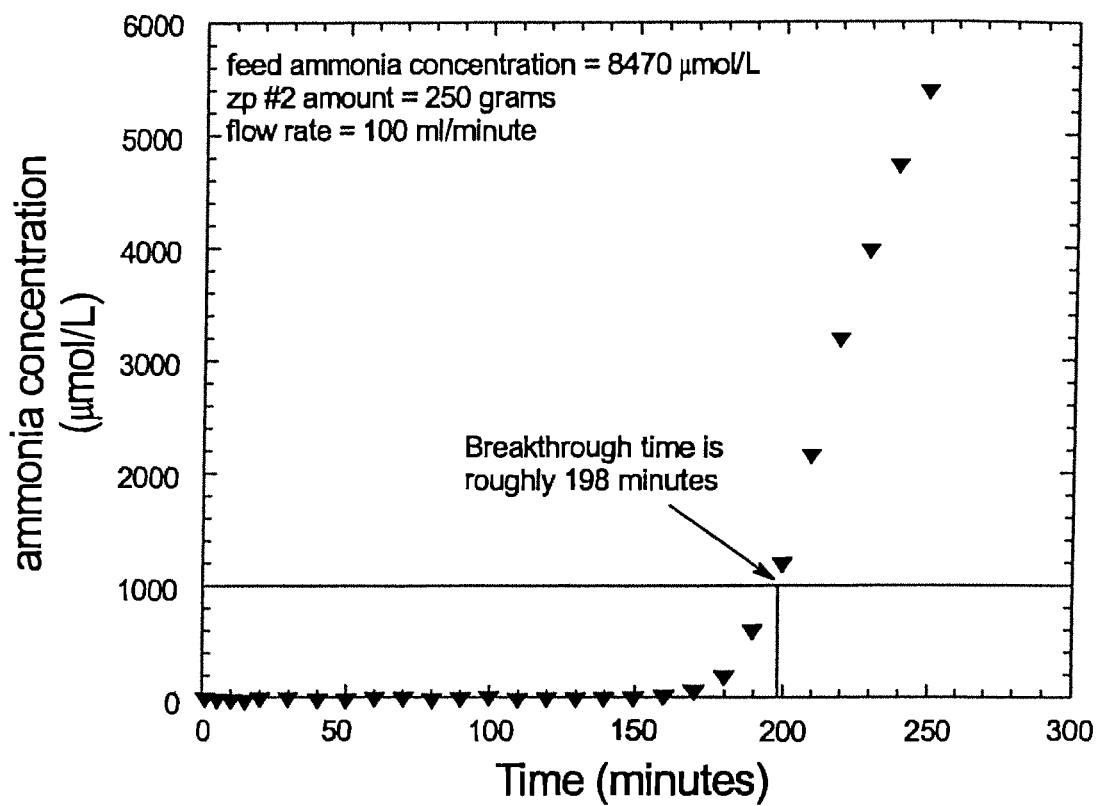

Experiments were conducted using urease, zirconium phosphate, and zirconium oxide in the same experimental set-up as above. Multiple columns were connected in series, with the zirconium oxide column added to the system after the cation column. The results for a test using Altus 271-6 urease, zirconium phosphate modified to a pH of 7.2 and zirconium oxide are set forth below in FIGS. 8-10. Note that the sodium balance is well maintained over the course of the test, which is a result of zirconium oxide removing sodium from the solution to counterbalance sodium released by the zirconium phosphate layer. Effluent pCO$_2$ levels are also significantly lower in the presence of zirconium oxide. Modified zirconium oxide captures sodium, and helps maintain the sodium balance over the course of the test. The test show that zirconium phosphate modified to a pH of 7.1-7.2 performs much better than those modified to a higher pH.

Experiment No. 3

Figure 11:
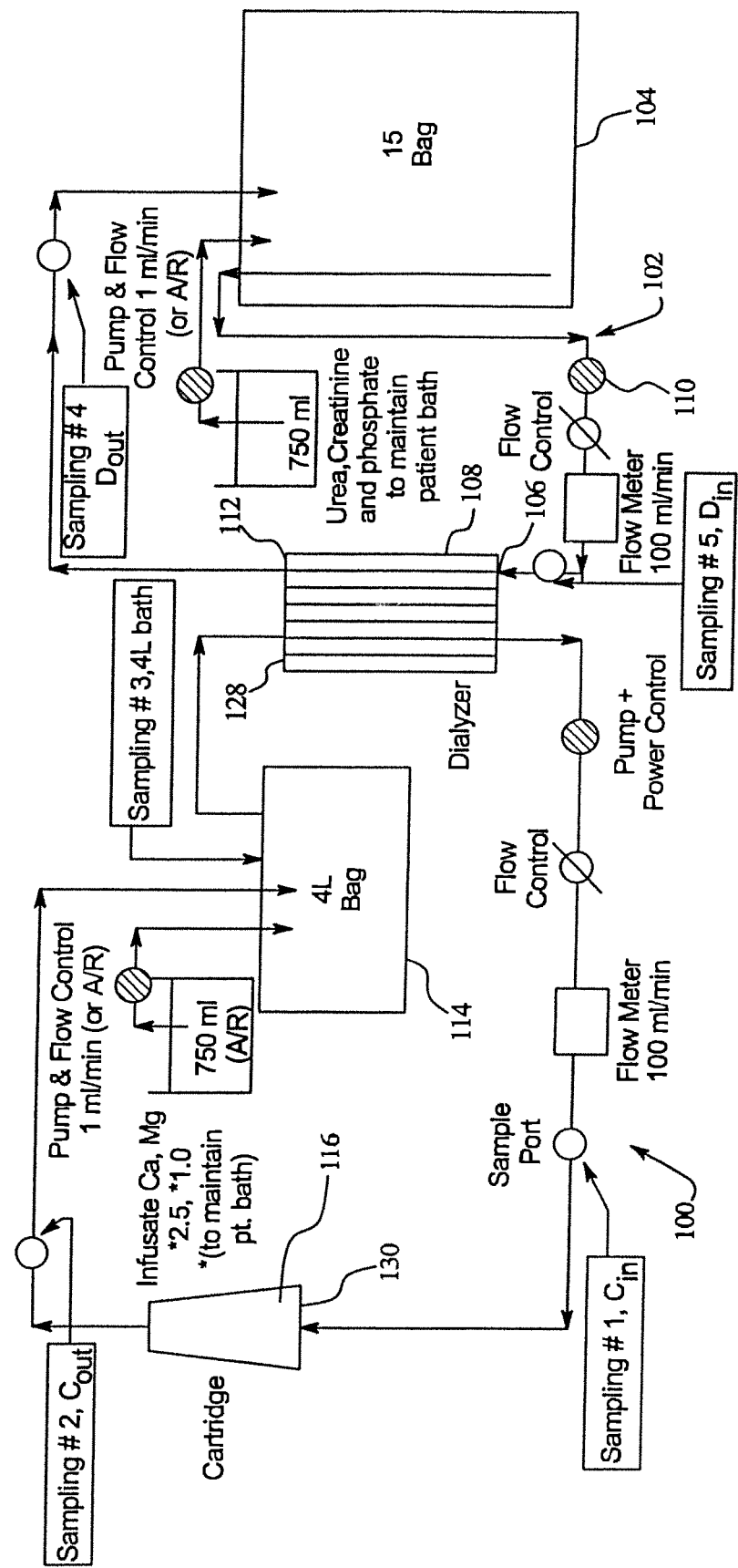
FIG. 11 illustrates the system that was used in Experiment No. 3 for testing the cartridges of the present disclosure.

Experimental Setup:
FIG. 11 illustrates a schematic of the experimental setup used in a study to evaluate the use of ion exchange resins in peritoneal dialysis setting. The set up included two loops 100 and 102. A 15-liter bag 104 representing the total fluid body of a patient was used in the second loop 102 of the setup. Although utilizing a 40-liter bag may make a more accurate estimation of the patient body, a 15-liter bag was used due to ease of analysis. The fluid from the 15-liter bag was pumped into the lumen side 106 of the dialyzer 108 at a flow rate of 100 mL/min using a pump 110. From the outlet 112 of the lumen side 106 of the dialyzer 108, the fluid returned to the 15-liter bag 104. Concurrently, as this fluid was returning into the 15-liter bag 104, it was infused with urea, creatinine, and phosphate, at 1 mL/min, to represent the total amount of wastes being generated continuously by the patient. The 15-liter bag 102 was maintained at a constant concentration of urea-nitrogen (20 mg/dL), creatinine (6 mg/dL), and phosphate (3.1 mg/dL). The initial feed solution contains 25 mmol/L of bicarbonate, 138 mEq/L of sodium, 2.5 mEq/L of calcium and 1.0 mEq/L of magnesium.

A 4-liter bag 114 containing sodium at 132 mEq/L, calcium at 2.5 mEq/L, magnesium at 1.0 mEq/L and bicarbonate at 25 mmol/L in DI water is provided. Initially the 4-liter solution is used to prime the dialyzer 108 and a cartridge 116. As the solution exits the cartridge 116, all the toxins and also calcium and magnesium, are completely removed. Accordingly, fluid returning to the 4-liter bag 114, is infused with calcium and magnesium so as to maintain the calcium and magnesium balance in the 15-liter bag 114. Both the 4-liter 124 and the 15-liter 114 bag were well mixed and the dialyzer 118 was operated at close to zero ultra filtration.

From the 4 L bag 114, the solution flows into the shell side 128 of the dialyzer 108. The urea creatinine and phosphate diffuses from the lumen side 116 of the dialyzer 108 to the shell side 128. The solution that exits the dialyzer 108 and enters the cartridge 116 has a urea nitrogen concentration of 10 mg/dL, Creatinine concentration of 3 mg/dL and phosphate 1 mg/dL. The flowrate on either side of the dialyzer 38 is maintained at 100 ml/mm.

The cartridge 116 was constructed as set forth above. Urea creatinine and phosphate flows to the bottom 130 of the cartridge 116, which contains urease, various ion exchange resins, and carbon. As noted above, urease is an enzyme whose function is to convert toxic urea into ammonium and carbon dioxide, is the first layer in the cartridge. The middle layer comprises of two different types of ion exchange resins, zirconium phosphate (zirconium phosphate) and zirconium oxide (zirconium oxide). Zirconium phosphate, as noted above, mainly removes ammonium ions, calcium, and magnesium from the solution, while releasing hydrogen and sodium. The zirconium oxide resin removes the phosphate. Finally, a carbon layer is used to remove creatinine, uric acid, and other organics from the solution. From the top of the cartridge, fluid is then directed back into the original 4-liter bag 114.

Pursuant to this study, samples were taken at 5 different points in the above setup. Sample "1" (C$_{IN}$) was taken before the fluid enters the cartridge inlet; Sample "2" (C$_{OUT}$) was taken as the sample exits after the cartridge; Sample "3" (4 L) was taken directly from the outflow of the 4-liter bag; Sample "4" (D$_{OUT}$) was taken as the fluid comes out of the lumen of the dialyzer; Sample "5" (D$_{IN}$) represents the fluid before entering the lumen inlet of the dialyzer. The sample D$_{IN}$ was taken from the 15 L bag 34, which is essentially well mixed and represents 15 L patient.

Figure 12C:
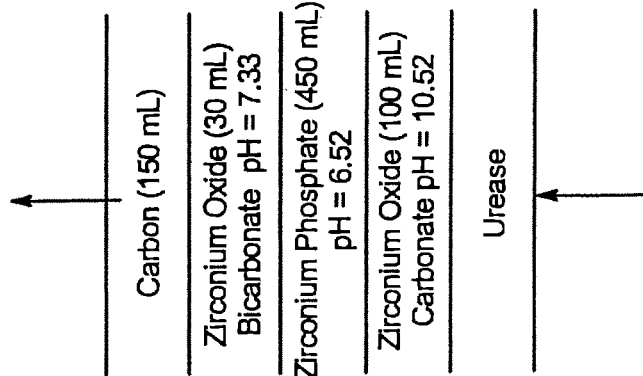
FIGS. 12a-c illustrate a cross-sectional view of the layers of the cartridge used in Experiment No. 3.
Figure 12B:
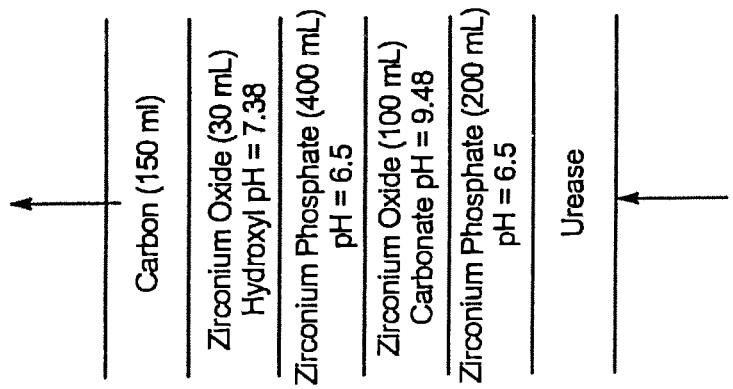
Figure 12A:
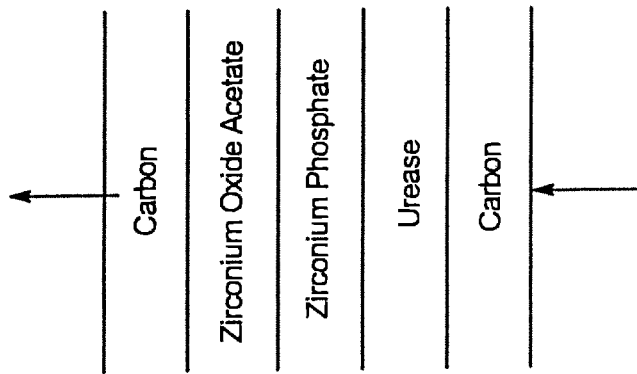
Figure 13A:
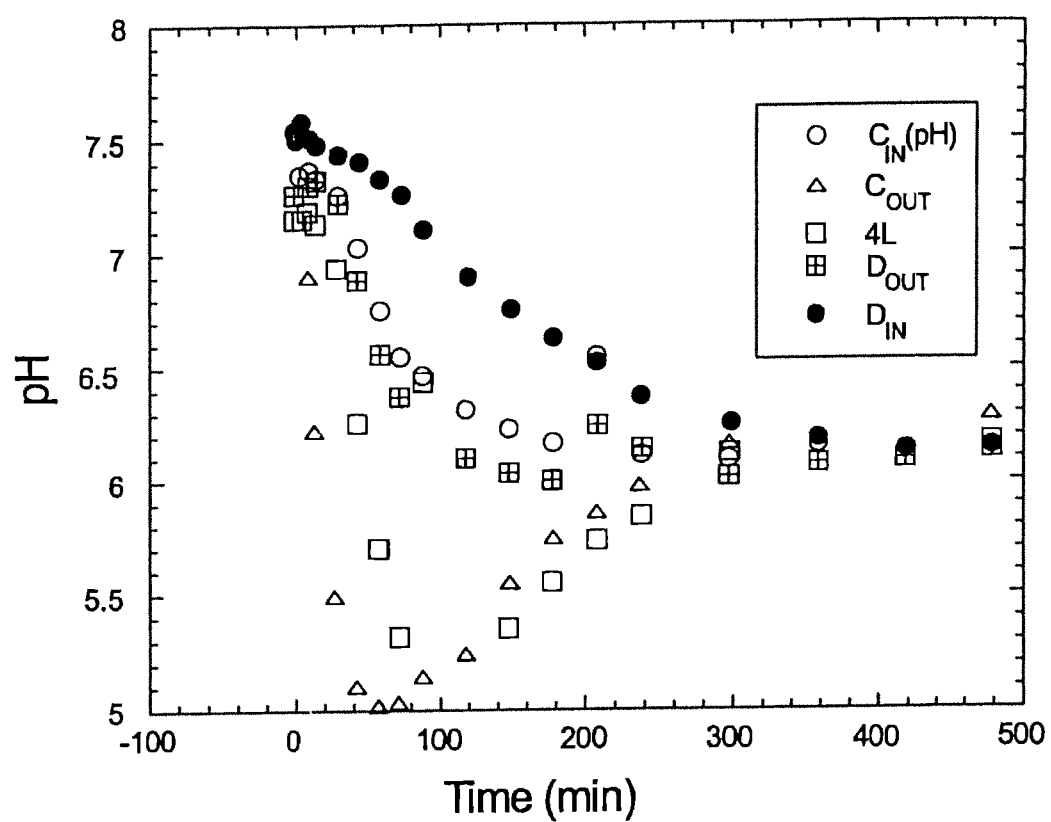
FIGS. 13a-c illustrate pH, sodium bicarbonate profiles of samples taken pursuant to Experiment No. 1.
Figure 13B:
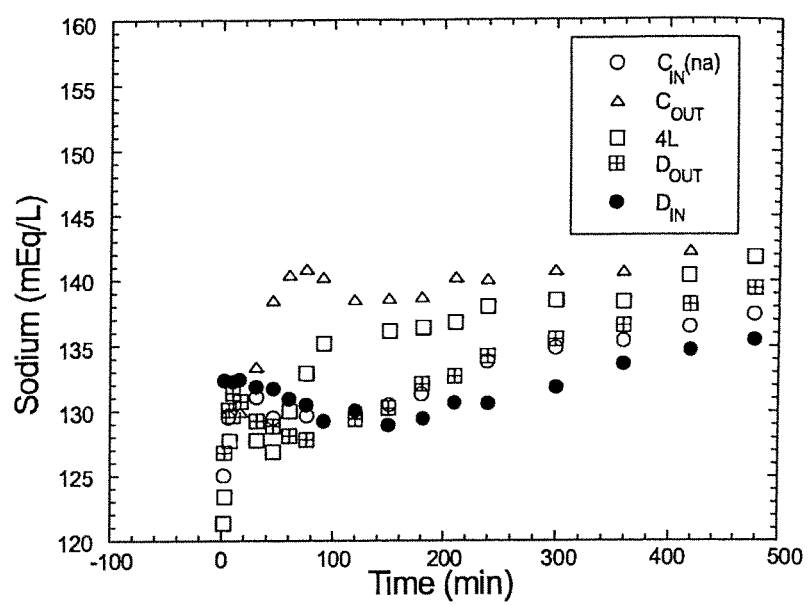
Figure 13C:
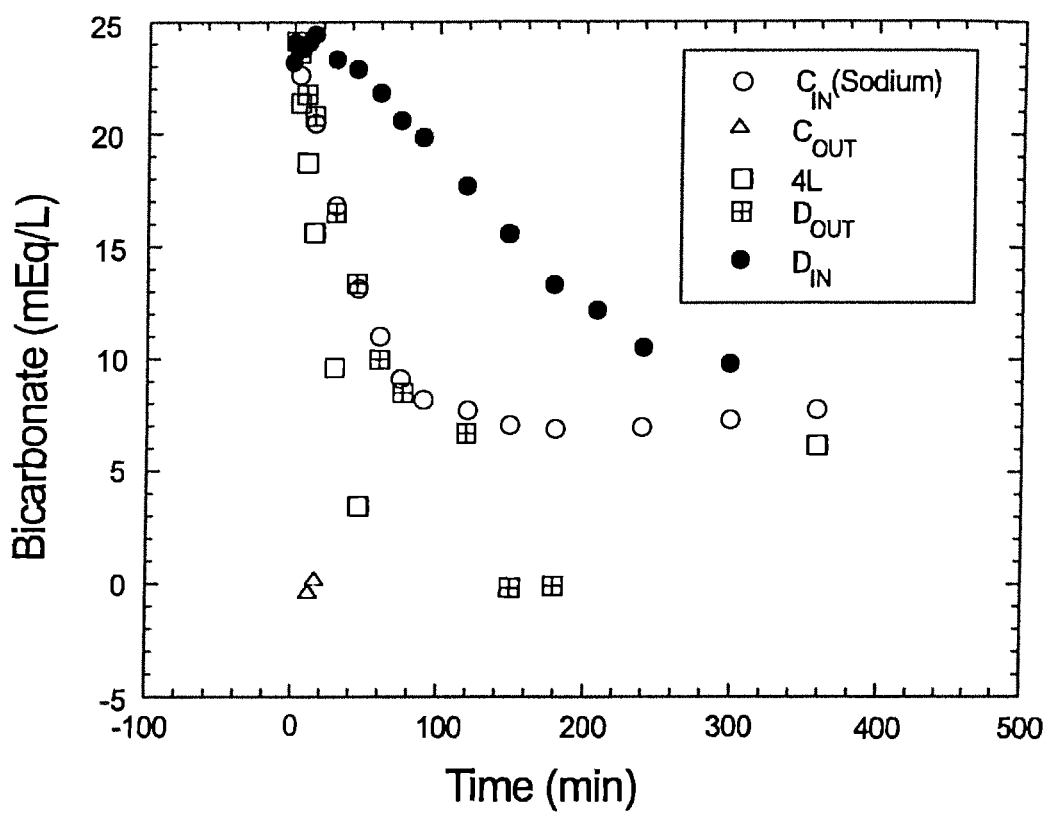

The above experimental setup was used to evaluate an embodiment of the cartridge of the present disclosure. A Redy Cartridge was obtained from Sorb Technology and used in the above experimental setup. FIG. 12 shows the various layers in the cartridge. FIG. 12a represents the Redy Cartridge, FIG. 12b represents the Redy Cartridge 1 and FIG. 12c represents the Redy Cartridge 2. The urea, creatinine and phosphate diffuse from 15 L patient bag across the dialyzer to the bottom of the cartridge. Five samples were taken from various locations as shown in FIG. 11. Samples were analyzed for pH, bicarbonate and sodium onsite. Analysis for urea, creatinine, phosphate, calcium, magnesium, chloride, lactate, and glucose were also carried out. FIGS. 13a, 13b, 13c show the pH, sodium and bicarbonate profiles. The pH in the 15 L patient bath drops from 7.546 to 6.156, bicarbonate drops from 23.2 to 0.0, sodium increases from 132.4 mEq to 135.3 mEq.

Instead of providing bicarbonate to the patient, bicarbonate is removed and sodium added. Also the pH drops and $pCO_2$ increases. Table 4 summarizes the pH, sodium, and bicarbonate profile from this study. Overall, 44 mEq of sodium was added and all of the bicarbonate was removed. This was a net gain of 125 mEq of sodium. The cartridge does remove urea, creatinine and phosphate completely, but does not satisfy the electrolyte requirement. Thus the resins or the cartridge cannot be used in peritoneal dialysis closed loop setting or in hemodialysis applications, it cannot be used unattended. Several different combinations were evaluated that could satisfy the requirement criteria for use in the cartridge for continuous recirculation of peritoneal dialysis solution. Some of the combinations were as follows:

1—Zirconium oxide in bicarbonate form at a pH of 8.85 used with zirconium phosphate (pH=6.2) in its standard form. In this setup there were only 4 layers.

2—Zirconium phosphate with a pH of 6.5 along with zirconium oxide in the bicarbonate form at two different pHs of 10.52 and 7.33. At the higher pH, bicarbonate should be in the form of carbonate.

3—Zirconium phosphate at a pH of 6.5 was used the bicarbonate form of zirconium oxide at a pH of 9.35 and 9.83 and the hydroxyl form of the zirconium oxide at a pH of 7.14 and 7.23.

4—Zirconium phosphate at a pH of 6.49 used along with zirconium oxide in the bicarbonate form at a pH of 8.80. In this case also there were 4 layers.

5—Since zirconium oxide is an amphoteric resin, this resin needs to adsorb the $Ca^{++}$ and $Mg^{++}$ ions, allowing the reduction of zirconium phosphate volume to 450 ml.

FIGS. 12b and 12c represents two alternatives from the various alternatives discussed.

FIG. 12b and FIG. 12c shows the modified cartridge in the study. From equilibrium adsorption isotherm studies it was shown that at a concentration of 10 mg/dl urea nitrogen in the peritoneal dialysis solution a 600 ml resin column is required. Therefore the size of the resin in Cartridge I (FIG. 6b) is 600 ml. In FIG. 2b, (cartridge I) the $1^{st}$ layer is urease, $2^{nd}$ layer is zirconium phosphate (pH=6.5, volume=200 mL), $3^{rd}$ layer is zirconium oxide in carbonate form (pH=9.48, volume=100 mL), $4^{th}$ layer is zirconium phosphate (pH=6.5, volume=400 mL) and $5^{th}$ layer is Zirconium oxide in the hydroxyl form (pH=7.38, volume=30 mL) the last layer is carbon. The zirconium oxide $3^{rd}$ (High pH) is used not only to adsorb the cations, but it can also raise the pH of the zirconium phosphate resin. The counter ions used in this resin could be bicarbonate, carbonate or hydroxyl. This layer adsorbs the calcium, magnesium, thus reducing the size of the zirconium phosphate layer as it is used only to adsorb ammonia. Phosphate is also adsorbed in this layer along with the other cations. The $5^{th}$ layer is zirconium oxide (pH=7.38) is used to adsorb phosphate and some sodium. But if there is no leaching of phosphate from the zirconium phosphate resin, this layer will not be required. The last layer is carbon, which again, can be placed anywhere.

Figure 14A:
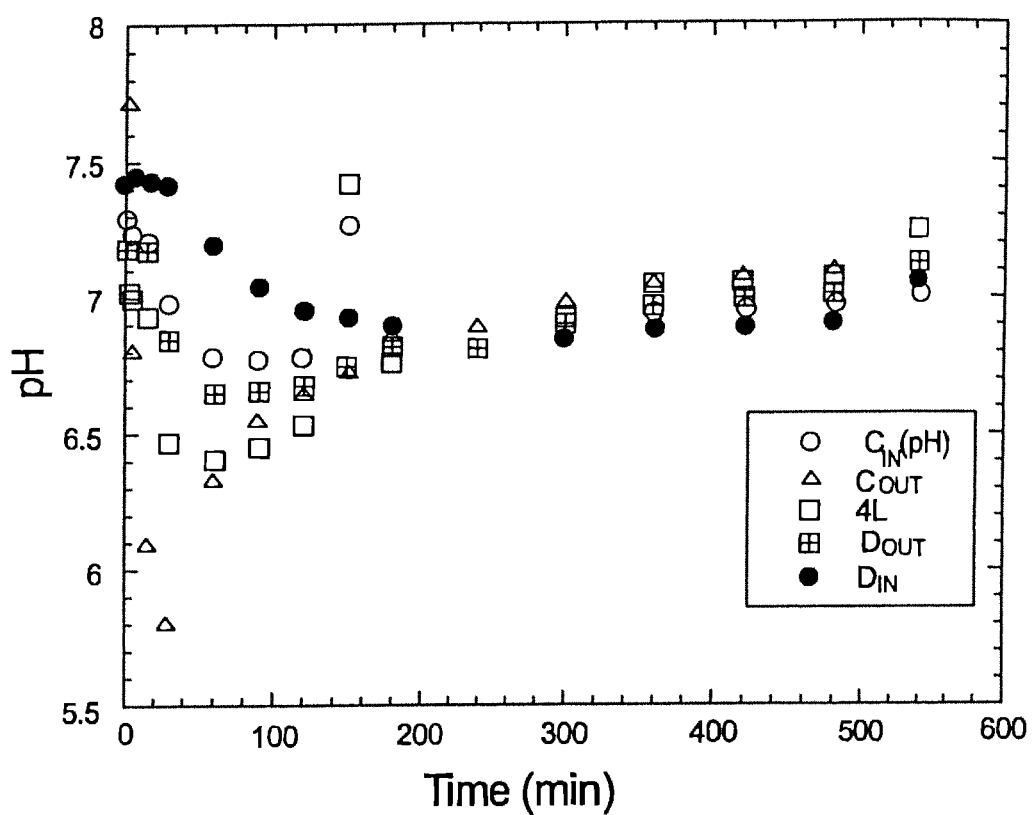
FIGS. 14a-d represent pH, sodium bicarbonate profiles of samples taken pursuant to Experiment No. 1.
Figure 14B:
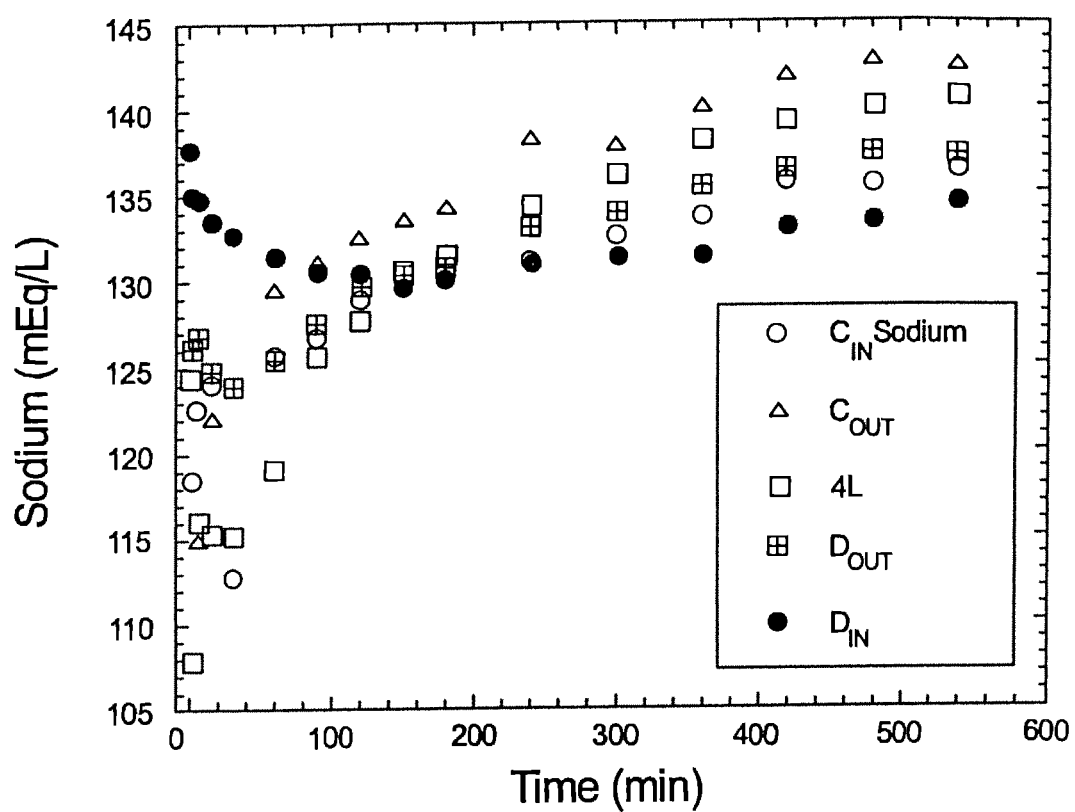
Figure 14C:
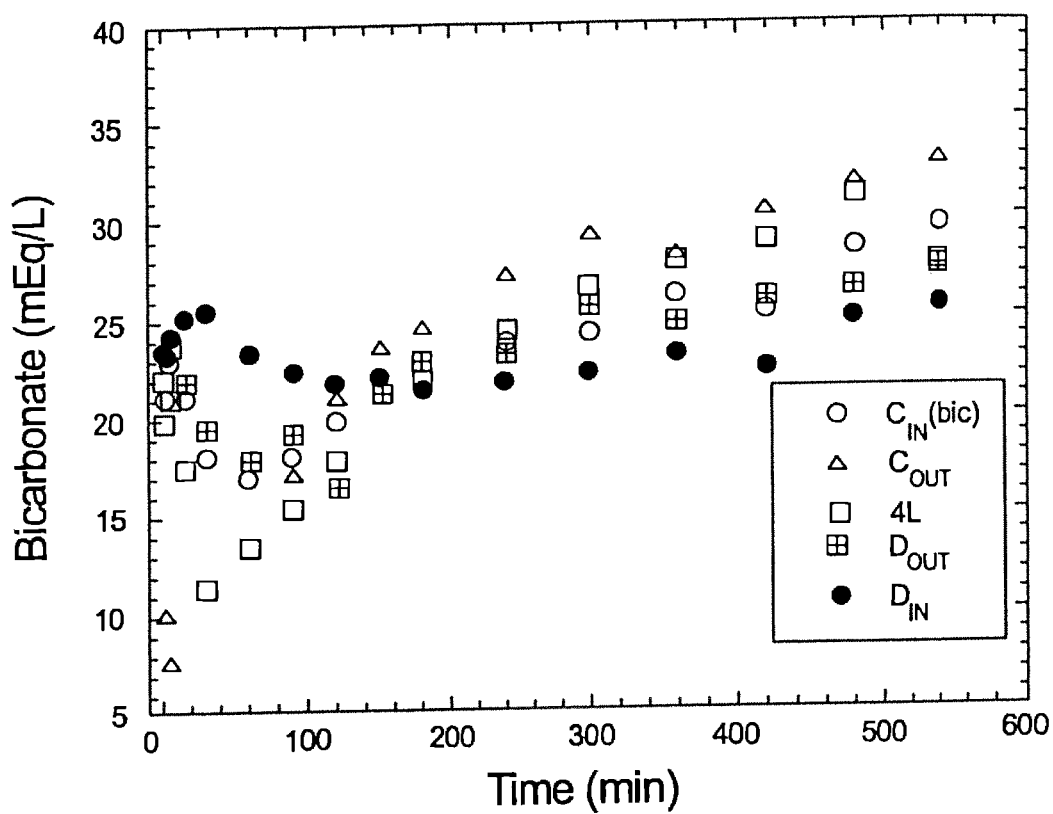
Figure 14D:
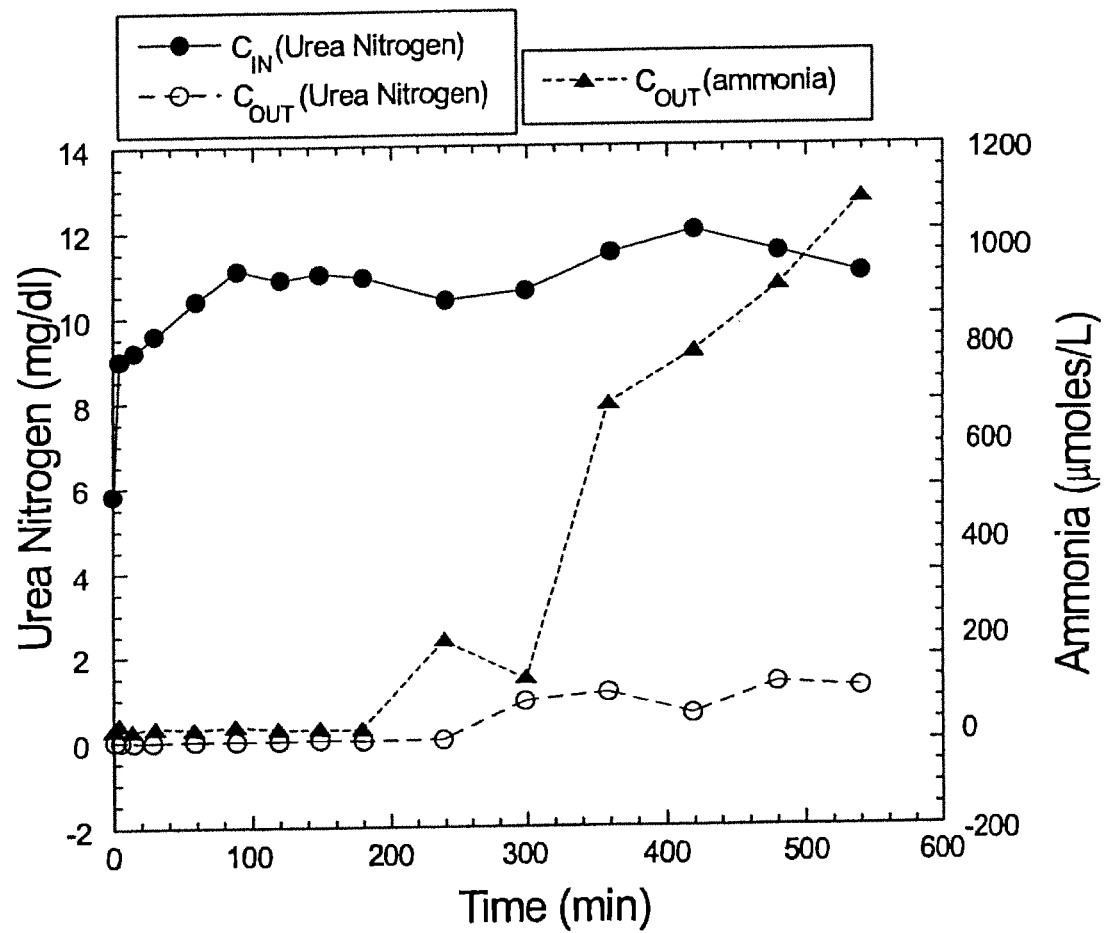

FIGS. 14a, 14b & 14c represent the pH, sodium bicarbonate and profile over the entire therapy time. Table 5 summarizes the pH, bicarbonate and sodium profile. The pH in the 15-liter patient bag goes from 7.49 to 6.9. Sodium is removed from the patient (15-liter bag) approximately 57 mEq is removed. The resins are designed such that it removes sodium initially for approximately 20 minutes or so, and then the cartridge slowly adds the sodium back. Similar trend is observed in the case of bicarbonate, also approximately 22.5 mEq of bicarbonate is added back to the 15-liter patient. In this experiment, as shown in FIG. 14d 4.94 gm of urea nitrogen is processed (10.6 gm of urea) which produces 353 mmol/L of ammonia and 176 mmol of bicarbonate. In the Redy cartridge run 124 mEq of sodium was added, but in our cartridge of the present disclosure only 5 mEq of sodium is added back into the circulation. In the cartridge of the present disclosure, the net bicarbonate gain was approximately 59 mEq. But in the cartridge run bicarbonate was completely removed. The pH in the 15-liter patient loop went down to 6.15 and all the bicarbonate was removed.

Figure 10:
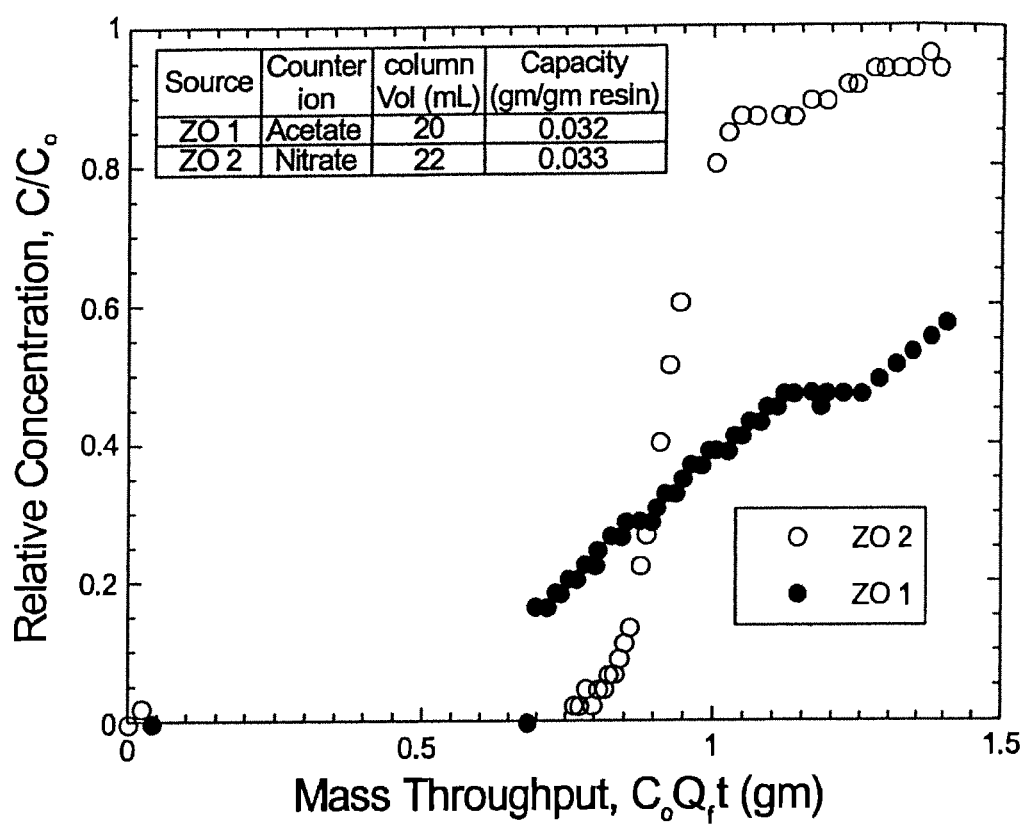

FIG. 12c shows the cartridge II used in the experimental setup described in FIG. 10. The amount of zirconium phosphate was reduced to 450 ml. Layers 2 and 4 were zirconium oxide in carbonate and bicarbonate form at pH of 10.52 and 7.33. Table 6 summarizes the results from this run. In this run, the pH of the zirconium oxide in layer 2 was higher so that it has better capacity for cations. Around 97.5 mEq of sodium was removed from the 15-liter patient bag and 15 mEq of bicarbonate was removed. There was net removal of 62 mEq of sodium. An addition of 5 mEq of bicarbonate in the stream. The bicarbonate profile can be improved in this run. Here we have also reduced the amount of zirconium phosphate to remove the same amount of urea.

Figure 15A:
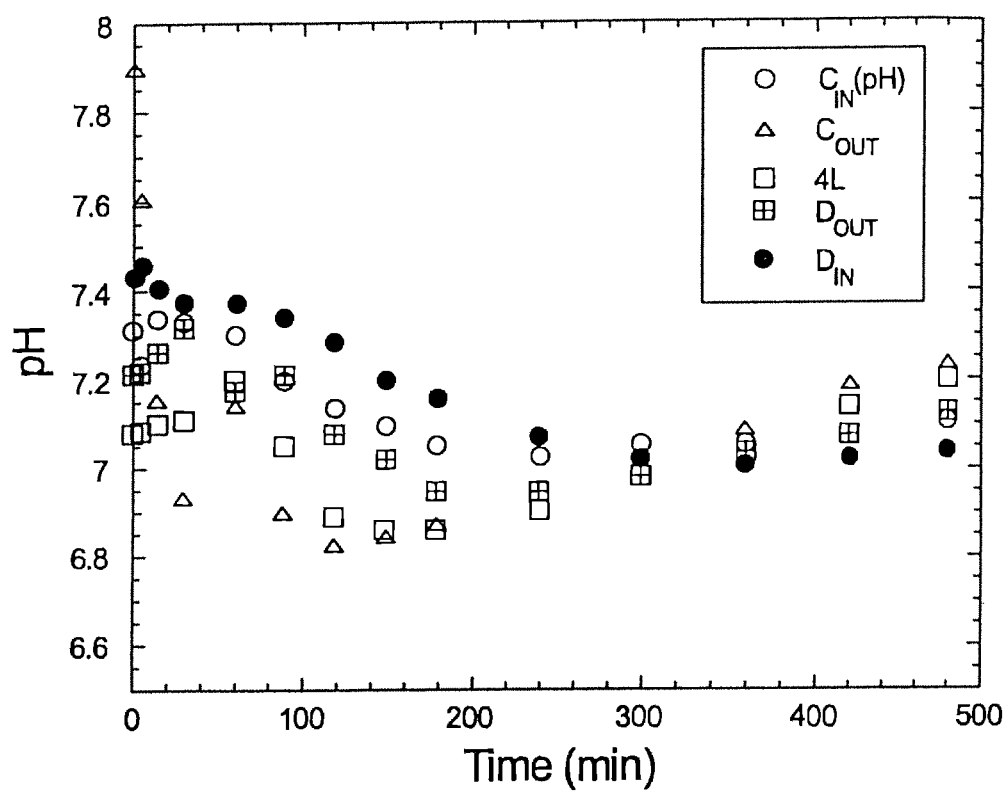
FIGS. 15a-c illustrate pH bicarbonate and sodium profiles of samples over time pursuant to Experiment No. 1.
Figure 15B:
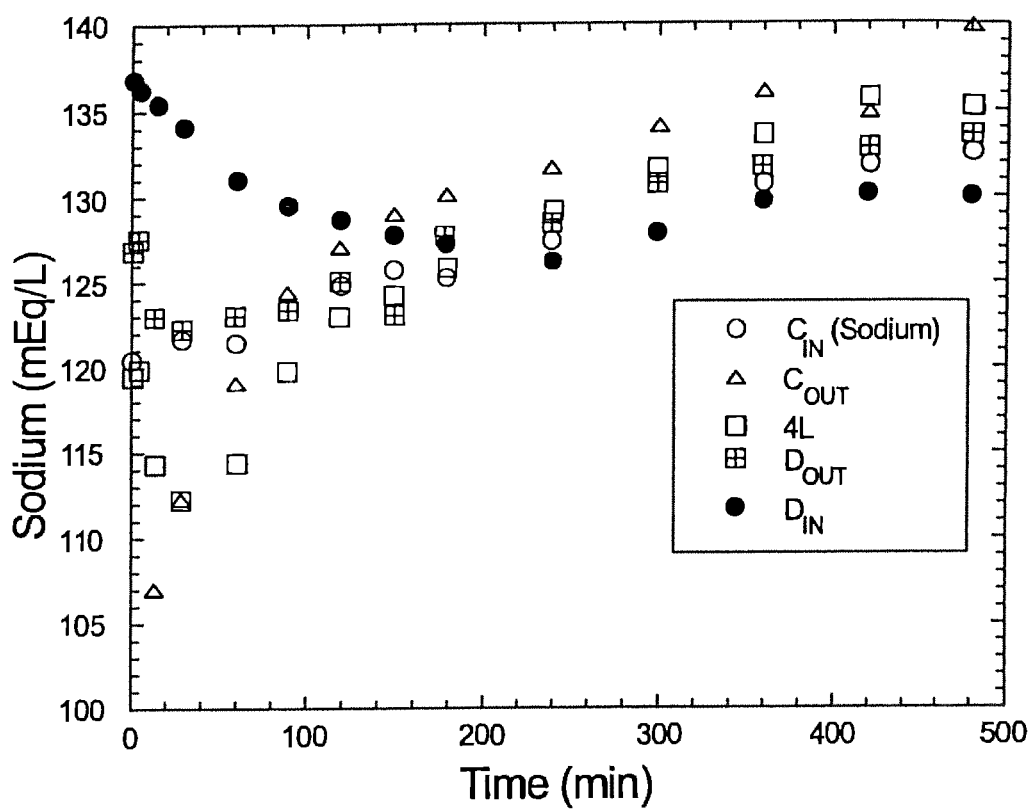
Figure 15C:
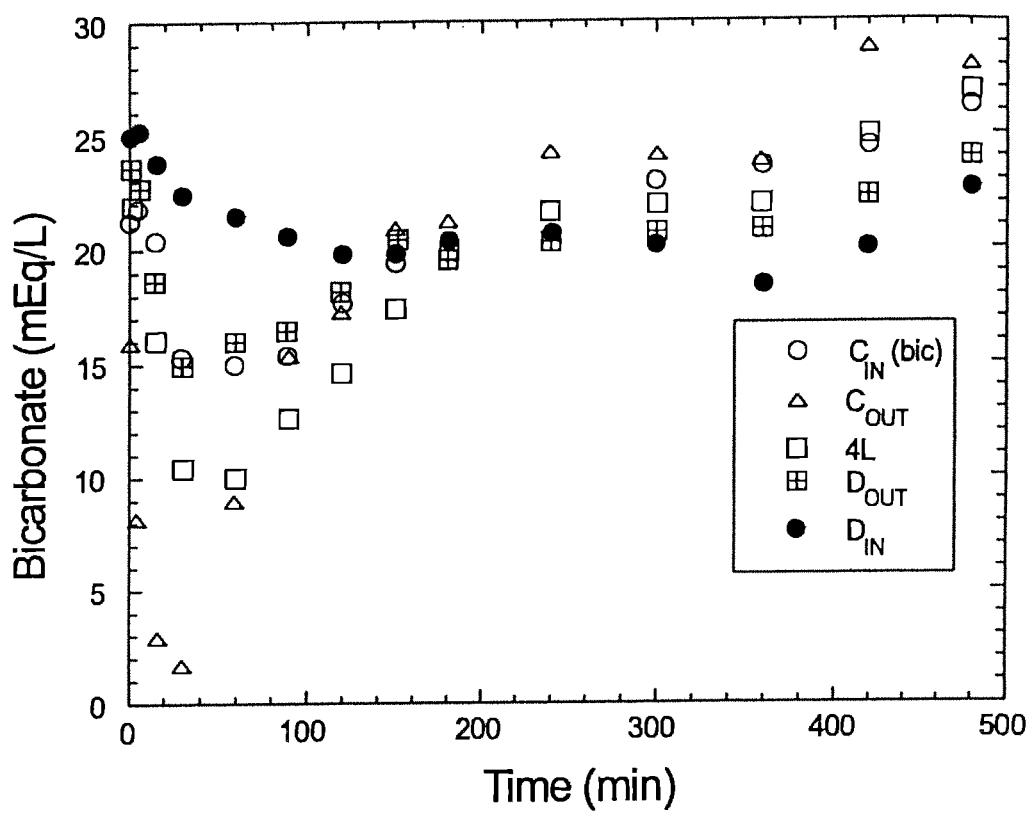
Figure 15D:
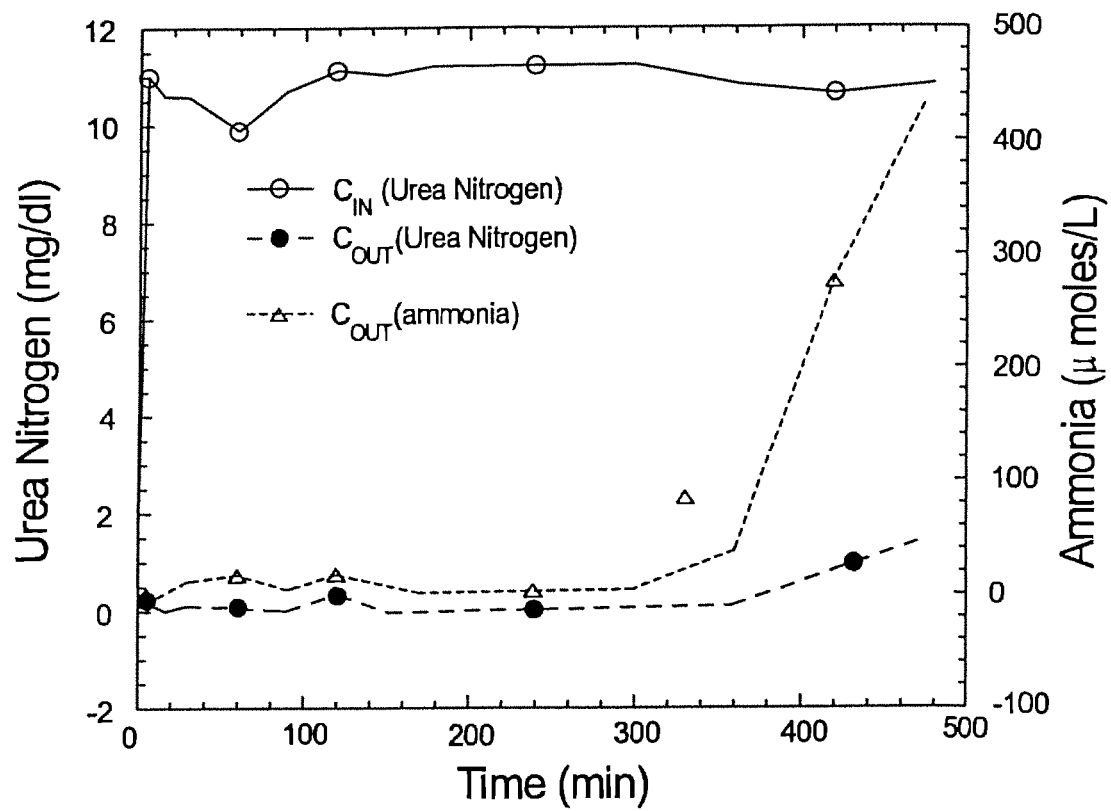
FIG. 15d illustrates the urea conversion over time pursuant to Experiment No. 1.

FIGS. 15a, 15b and 15c shows the pH bicarbonate and sodium profile over the entire therapy time. FIG. 15d shows the urea conversion. In this experiment a higher pH of the bicarbonate resin was utilized and also the zirconium phosphate resin was only 450 ml.

TABLE 5

Summary of Cartridge Test

| Time (Min.) | | Cartridge | | 4-Liter Bag | Gain/Loss 4-liter Bag (mEq) | 15-Liter | | Gain/Loss 15-Liter Bag (mEq) |
| --- | --- | --- | --- | --- | --- | --- | --- | --- |
| | | In | Out | | | In | Out | |
| 0 | pH | — | — | 7.147 | — | 7.546 | — | — |
| 480 | pH | 6.153 | 6.3 | 6.17 | — | 6.14 | — | 6.156 |
| 0 | Sodium (mEq/L) | — | — | — | — | 132.4 | — | — |
| 480 | Sodium (mEq/L) | 137.3 | 166.3 | 141.7 | 81.2 | 135.3 | 139.3 | 43.5 |
| 0 | Bicarbonate (mEq/L) | — | — | 23.2 | — | 23.1 | — | — |
| 480 | Bicarbonate (mEq/L) | — | — | — | — | 10 | — | — |

TABLE 6

Summary Cartridge 1

| Time (Min.) | | Cartridge | | 4-Liter Bag | Gain/Loss 4-liter Bag (mEq) | 15-Liter | | Gain/Loss 15-Liter Bag (mEq) |
|---|---|---|---|---|---|---|---|---|
| | | In | Out | | | In | Out | |
| 0 | pH | — | — | 6.99 | — | 7.49 | — | — |
| 480 | pH | 6.9 | 7.09 | 7.06 | — | 6.9 | 6.997 | — |
| 0 | Sodium (mEq/L) | — | — | 124.4 | — | 137 | — | — |
| 480 | Sodium (mEq/L) | 135.4 | 142.6 | 139.9 | 62 | 133.2 | 137.2 | 57 |
| 0 | Bicarbonate (mEq/L) | — | — | 22 | — | 23.4 | — | — |
| 480 | Bicarbonate (mEq/L) | 28.4 | 31.8 | 31.1 | 36.4 | 24.9 | 26.4 | 22.5 |

TABLE 7

Summary Cartridge II

| Time (Min.) | | Cartridge | | 4-Liter Bag | Gain/Loss 4-liter Bag (mEq) | 15-Liter | | Gain/Loss 15-Liter Bag (mEq) |
|---|---|---|---|---|---|---|---|---|
| | | In | Out | | | In | Out | |
| 0 | pH | — | — | 7.08 | — | 7.42 | — | — |
| 480 | pH | 7.106 | 7.235 | 7.2 | — | 7.036 | 7.122 | — |
| 0 | Sodium (mEq/L) | — | — | 126 | — | 136.60 | — | — |
| 480 | Sodium (mEq/L) | 132.6 | 139.9 | 135.3 | 37.2 | 130.1 | 133.7 | 99 |
| 0 | Bicarbonate (mEq/L) | — | — | 22 | — | 23.5 | — | — |
| 480 | Bicarbonate (mEq/L) | 26.2 | 28 | 26.9 | 19.6 | 22.5 | 24 | −15 |

Figure 16:
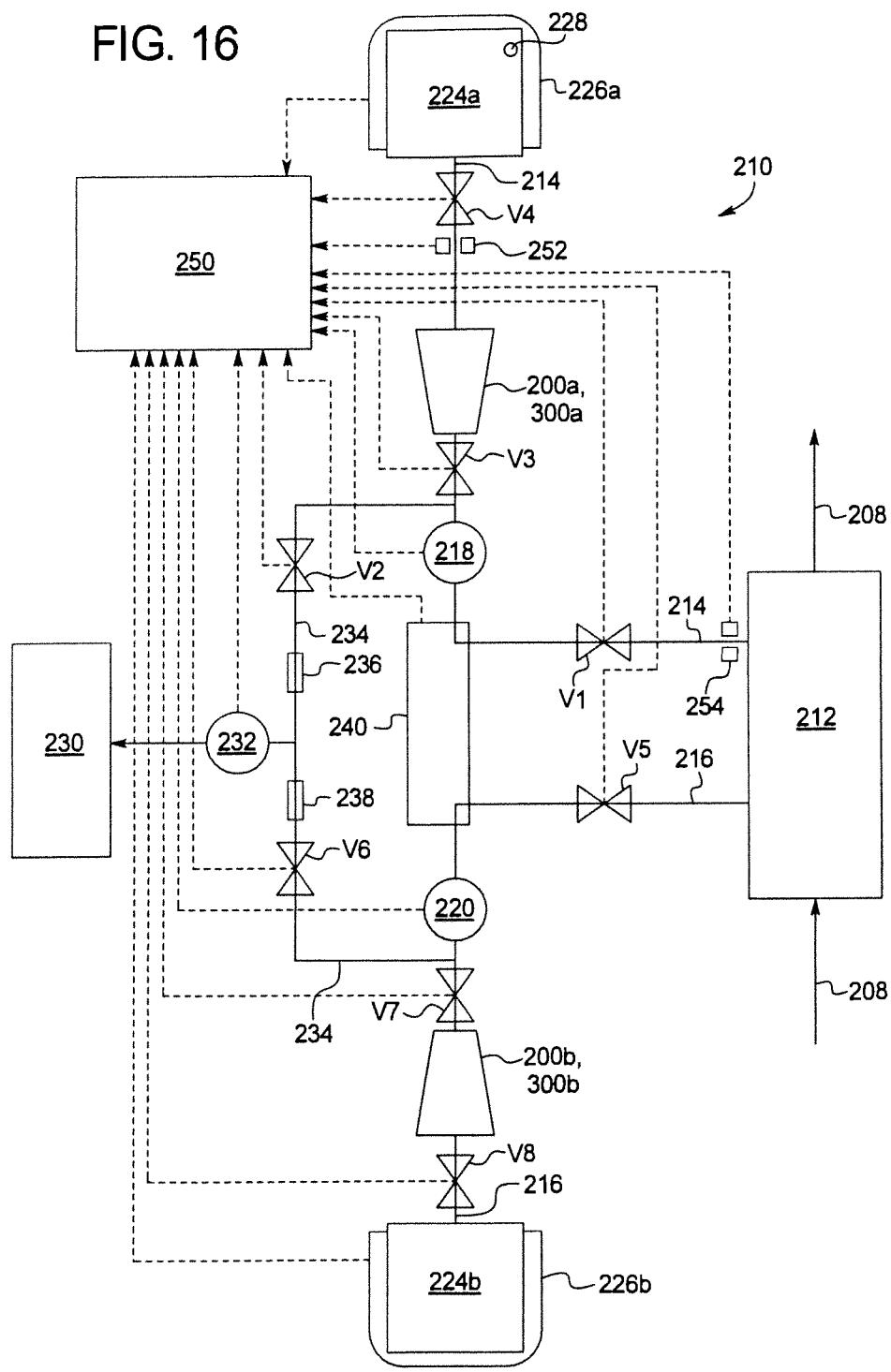
FIGS. 16, 17, 18a, 18b and 19 illustrate additional systems and methods of the present disclosure.
Figure 17:
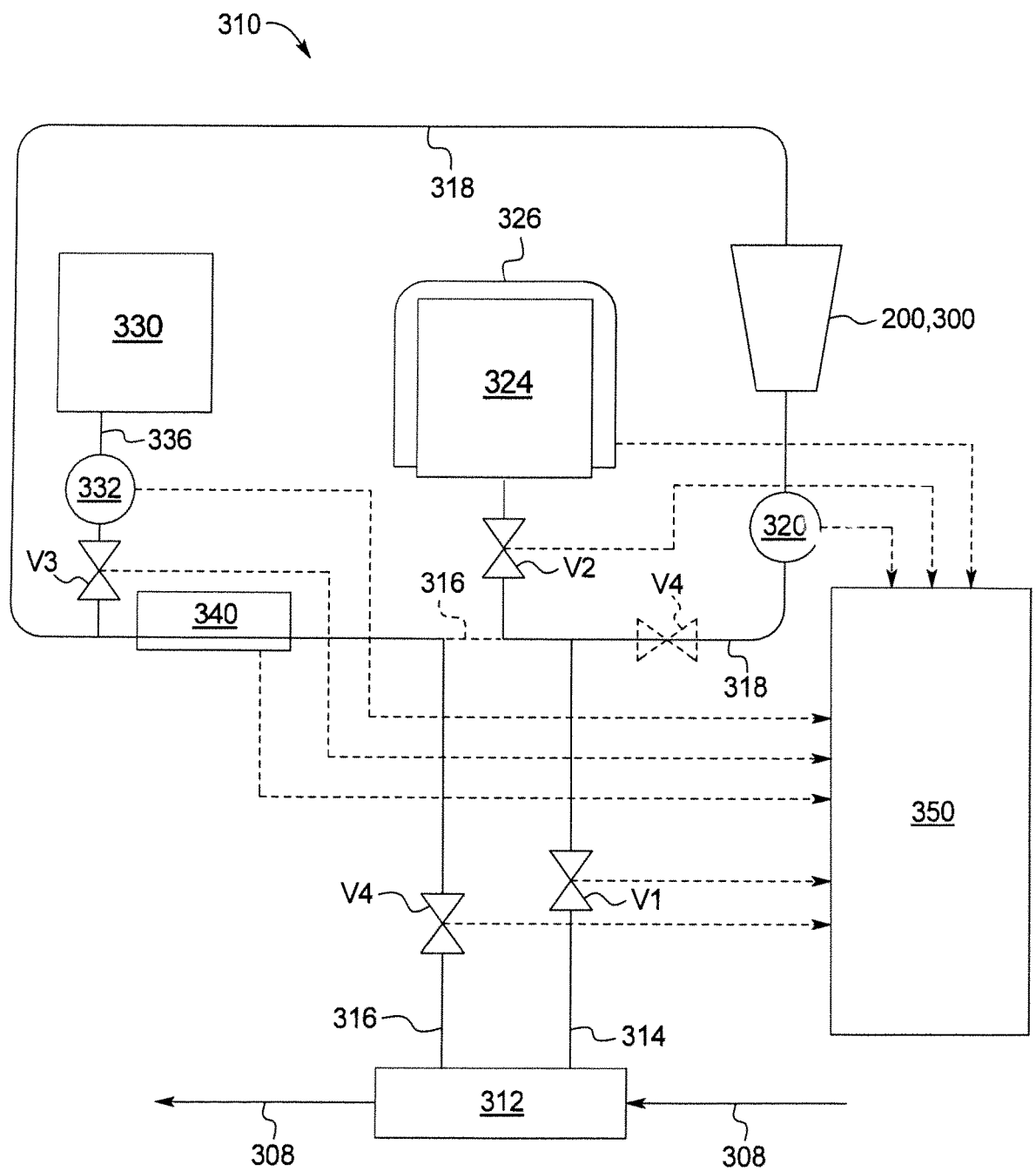

Referring now to FIGS. 16, 17, 18a and 18b, systems 210 and 310 for passing spent dialysis fluid through a sorbent cartridge multiple times before returning cleansed fluid to the patient or dialyzer are illustrated. In general, system 210 of FIG. 16 illustrates a back-and-forth embodiment, while system 310 of FIG. 17 illustrates a multiple pass or cycle embodiment. Either system 210 or 310 can be used for hemodialysis ("HD"), hemofiltration ("HF"), hemodiafiltration ("HDF") or peritoneal dialysis ("PD"). Either system 210 or 310 can employ any of the sorbent cartridges described herein, including cartridges 200 and 300 illustrated below in FIGS. 18a and 18b.

In FIG. 16, system 210 includes a dialyzer 212 (for hemodialysis and hemodiafiltration). Dialyzer 212 is alternatively a hemofilter for hemofiltration or the patient's peritoneum for peritoneal dialysis. For ease of description, filter 212 will be referred to as a dialyzer but includes a hemofilter or any other type of blood filter as well as the patient's peritoneum. Dialyzer 212 can be used with PD, where sterile PD solution flows through lines 208 (marked blood in FIG. 16) instead of blood for HD, HF or HDF. The sterile PD solution flows from the patient's peritoneum, to dialyzer 212, back to the patient's peritoneum, and so on. PD dialysate running through lines 214 and 216 can but does not have to be sterile because the dialysate is separated from the sterile solution by the dialyzer membranes. Alternatively, dialyzer 212 is not used with PD. Here, dialyzer 212 is instead the patient's peritoneum and lines 214 and 216 instead run to a catheter, e.g., a dual lumen catheter, which is placed in sterile communication with the patient's peritoneum. In this latter embodiment, PD solution running through the patient's peritoneum, lines 214 and 216, and containers 224a and 224b are sterile.

As illustrated, dialyzer 212 (or the patient's peritoneum) is connected to dialysis fluid lines 214 and 216. Dialysis fluid line 214 is connected fluidly to pump 218, while dialysis fluid line 216 is connected fluidly to pump 220. Pumps 218 and 220 and any of the pumps described herein can be peristaltic pumps, membrane pumps, gear pumps or other suitable medical pump. If pumps 218 and 220 are membrane pumps, the pumps are surrounded by valves V1 to V3 (pump 218), V5 to V7 (pump 220), as illustrated, so that the membrane pumps, like peristaltic pumps, can be reversible and pump in either direction in lines 214 and 216. The surrounding valves enable pumps 218 and 220 to pull fluid in (negative pressure on membrane) and push fluid out (positive pressure on membrane) in either direction.

Figure 18A:
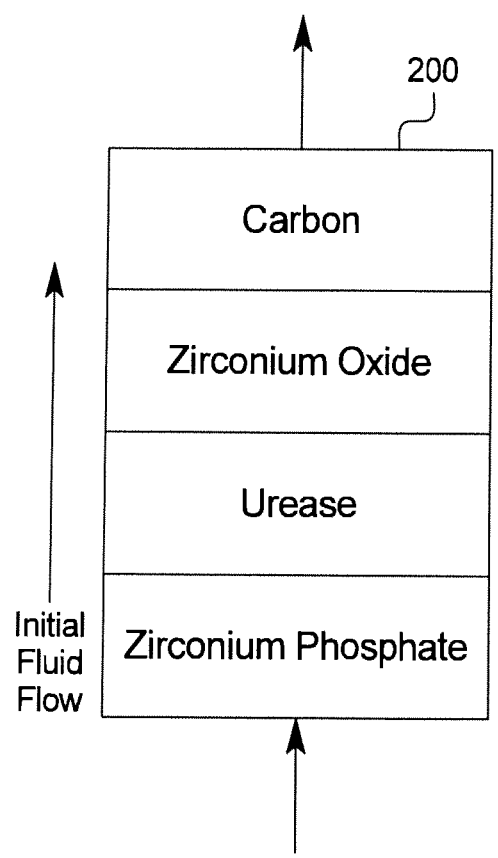
Figure 18B:
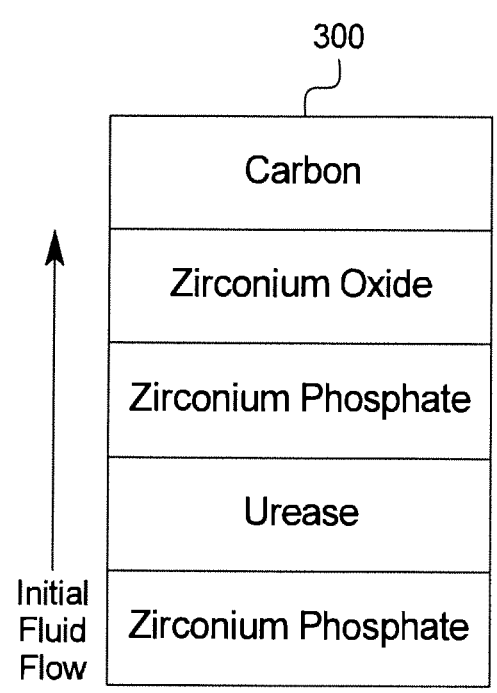

Pump 218 pumps to and from sorbent cartridge 200a, 300a and storage container 224a. Pump 220 pumps to and from sorbent cartridge 200b, 300b and storage container 224b. Cartridges 200a and 200b (if FIG. 18a is used, in which cartridges 200a and 200b are collectively or generally referred to as cartridge 200) can (i) be different sorbent cartridges, (ii) be the same sorbent cartridge or (iii) be the same sorbent cartridge divided into cartridge halves 200a and 200b. Sorbent cartridges 300a and 300b (if FIG. 18B is used, in which cartridges 300a and 300b are collectively or generally referred to as cartridge 300) can likewise (i) be different sorbent cartridges, (ii) be the same sorbent cartridge or (iii) be the same sorbent cartridge divided into cartridge halves 300a and 300b. Likewise, storage containers 224a and 224b can be different containers or be the same container divided into container halves 224a and 224b.

Heaters 226a and 226b are illustrated as batch heaters that batch heat containers 224a and 224b. Heaters 226a and 226b can be separate heaters or be the same heater having heating halves 226a and 226b. Heaters 226a and 226b (or heating halves) are alternatively inline heaters operating to heat dialysis fluid lines 214 and 216. Heaters 226a and 226b may additionally include a scale for weighing the contents within containers 224a and 224b.

An infusion solution container 230 is provided, which holds an infusion solution or infusate, which is generally sterilized, and which contains additives removed by sorbent cartridges 200, 300 that need to be added back in before the dialysate is returned to dialyzer or patient 212. The infusate may be different for blood and PD therapies, for example, infusate for PD may additionally contain glucose. An infusion solution pump 232 (peristaltic or membrane) meters infusion solution from supply 230 through tee'd infusion line 234 selectively via valves V2 and V6 to fluid lines 214 and 216, respectively. Alternatively, infusion solution pump 232 is not provided and flow restrictors 236 and 238 instead allow infusion solution to be gravity fed selectively via valves V2 and V6 to fluid lines 214 and 216, respectively, in a metered and controlled manner.

Dialyzer 212, sorbent cartridges 200, 300, dialysate bags or containers 224a, 224b and infusion supply bag or container 230 can be disposable and part of a disposable set having (i) pump actuation areas operable with the pumps 218, 220 and 232, and (ii) valve actuation areas operable with the valves V1 to V8. Certain parts of the disposable set, such as dialyzer 212 and the tubing of the set, may be disinfected after treatment for reuse. An analyzer unit 240 (discussed below) through which fluid lines 214 and 216 extend is in one embodiment reusable, as are control unit 250 (discussed below), heaters 226a and 226b (and possibly on accompanying weigh scales), the pump actuators for pumps 218, 220 and 232 and valve actuators for valves V1 to V8. Thus in one embodiment, system 210 has a disposable component and a reusable component.

Analyzer unit 240 includes probes and sensors, e.g., temperature compensated conductivity sensors, or otherwise samples fluid flowing through lines 214 and 216 for relevant parameters, such as any one or more of temperature, conductivity, ammonia, ammonium, glucose, electrolyte and pH. Analyzer unit 240 monitors the physical/chemical properties of the dialysis fluid leaving and entering the dialyzer or patient 212.

The dashed lines in FIG. 16 are electrical and/or electrical signal lines through which control unit 250 communicates electrically and operationally with each of the actuators of pumps 218, 220 and 232, the actuators of valves V1 to V8, heaters 226a and 226b (and possibly associated electronic scales) and analyzer unit 240. Control unit 250 includes one or more processor and memory that are programmed, configured and/or manipulated to run a hemodialysis, hemofiltration, hemodiafiltration or peritoneal dialysis sequence. Control unit 250 can further include the necessary battery/power components and I/O control for any of the different components of the particular dialysis therapy run on system 210.

For hemodialysis, one of containers 224a, 224b, e.g., container 224a, is initially full with bagged, sterile dialysis fluid, while the other container 224b is initially empty (but sterile). Containers 224a, 224b can be supported vertically or be inclined so as to trap sterile air at the top of the containers. Blood flows through the blood side of the dialyzer, while dialysis fluid is pumped via pumps 218 and 220 from container 224a, across dialyzer 212, though sorbent cartridge 200b, 300b and into container 224b. Pump 220 can be run controllably faster than pump 218 to remove a desired amount of ultrafiltrate ("UF") from the patient. Volume control, e.g., for UF control, can be effectuated by using scales with heaters 226a and 226b for weighing bags 224a and 224b. Here, for example, the initial weight X of unused dialysate is weighed in bag 224a. Control unit 250 runs pump 220 Y % faster than pump 218 to remove a desired amount, e.g., Z, of UF after the initial pass from bag 224a to 224b. When the weight of fluid in bag 224b reaches X plus Z, the first pass from bag 224a to 224b is considered to be completed. Control unit 250 is programmed in one embodiment to control pumps 218 and 220 to ensure that all of the fresh fluid from bag 224a is removed before or at the time when the weight of fluid in bag 224b reaches X plus Z.

Volume control, e.g., for UF control, can be effectuated alternatively by using known volume pumps, e.g., membrane pumps. Here, each pump stroke pumps a known volume. If volumetric pumps 218 and 220 have the same known volume, then UF can be controlled by stroking the downstream pump a number of additional times to remove a desired amount of UF per pass from bag 224a to bag 224b or vice versa. Here, for example, if the volume of unused dialysate is known to be one liter, control unit 250 runs pump 218 a first number of strokes to remove the one liter of fluid from bag 224a and runs pump 220 a second, larger number of strokes to push or pull one liter of used fluid plus a desired amount of UF for that pass into bag 224b. Volumetric control is achieved alternatively by counting revolutions of pumps 218 and 220, which are in this case peristaltic pumps. With volumetric control, scales at heaters 226a and 226b are not needed.

After the first pass when container 224a is sufficiently empty and container 224b is sufficiently full, control unit 100 causes the operation to reverse such that while blood flows through the blood side of dialyzer 212, dialysis fluid is pumped via pumps 218 and 220 from container 224b, in the reverse though sorbent cartridge 200b, 300b, across dialyzer 212, though sorbent cartridge 200a, 300a to container 224a. Here, pump 218 can be run controllably faster than pump 220 to remove a desired amount of UF, which is measured gravimetrically or volumetrically as described above. The cycle is then repeated, each time removing a desired increment of UF.

It should be appreciated that in each pass, spent dialysis fluid leaving dialyzer 212 (or the patient) is pushed first through one side (presenting zirconium phosphate first) of sorbent cartridge 200, 300 and then pulled in the reverse direction through the other side of sorbent cartridge 200, 300. After the second, reverse pass, the dialysis fluid is ready to be used again as fresh dialysis fluid through dialyzer 212.

In either the gravimetric or volumetric UF control embodiments, bags or containers 224a and 224b can be oversized enough to trap and hold a desired amount of UF. Alternatively, because one of the bags or containers is empty initially, that empty container can provide the additional space needed for UF. Here, partial deliveries from bags or containers 224a and 224b may be performed for each pass. For example, assume bags 224a and 224b are both one liter bags, bag 224a is initially full and bag 224b is initially empty. The initial pass from bag 224a to bag 224b can be 9/10 liter, leaving 1/10 liter in bag 224a. Assuming 1/10 liter of UF is gained over the pass, bag 224b becomes full with one liter of fluid (9/10 liter delivered plus 1/10 liter UF). In the return pass, 8/10 of a liter is flowed from bag 224b to bag 224a, leaving 2/10 liter in bag 224b. Assuming 1/10 liter of UF is gained over the pass, bag 224a becomes full with its residual 1/10 liter, 8/10 liter of returning dialysate plus 1/10 liter UF. The total fluid in system 210 has increased from one liter to 1.2 liters due to UF. But system 210 has a total capacity to hold two liters. In the next pass from bag 224a to bag 224b, 7/10 of a liter can be delivered, leaving 3/10 liter in bag 224a. Assuming 1/10 liter of UF is generated, bag 224b becomes full (7/10 liter delivered plus 2/10 liter residual plus 1/10 liter UF). Each delivery pass is decreased as illustrated above until both bags become full. The amount of UF removed from the patient for each pass can be adjusted to set a desired number of passes to obtain a desired clearance of waste and solutes from the patient.

For hemofiltration and hemodiafiltration, one or both of fluid lines 214 and 216 are branched (not illustrated) at dialyzer 212 to communicate additionally with blood lines 208. Additional valves are provided in the main and branch lines for both lines 214 and 216. Specifically for hemofiltration, fresh dialysis fluid flows through the branch line of line 214 or 216, directly to the upstream or downstream blood line 208, instead of to the dialyzer. Spent dialysis fluid is pulled from the hemofilter 212, through the other line 216 or 214, through the respective sorbent cartridge 200, 300 and to the respective container 224a, 224b. Hemodialfiltration is generally the same as hemofiltration, except that fresh dialysis fluid flows to both the dialyzer 212 and the upstream or downstream blood line.

As explained above, for peritoneal dialysis ("PD"), (i) blood in tubes 208 can instead be sterile dialysis fluid or (ii) dialyzer 212 can instead be the patient's peritoneum. In both of these alternatives, PD is or can be carried out under a continuous flow scenario ("CFPD") in which PD solution is continuously introduced and removed from the patient's peritoneum. In the second alternative (ii) in which dialyzer 212 is instead the patient's peritoneum, PD can alternatively be carried out under a batch or continuous cycling peritoneal dialysis ("CCPD") regime. Here, PD solution is delivered to the patient's peritoneum via line 214 or 216 but is not removed at the same time and is instead left to dwell within the patient. After a certain dwell period, all of the fluid from the patient's peritoneum is removed via the other of the lines 216 or 214, or a portion of the fluid is removed from the patient's peritoneum and is replaced by fresh fluid for tidal flow PD. Fluid still flows however back and forth between containers 224a and 224b.

In a third PD therapy alternative, half of system 210 can be discarded. Dialysis fluid flows either to the patient 212 or from the patient 212 at any given time, thus only line 214 or 216 (assume line 214 from here on out for ease of description) and associated sorbent cartridge, pump, valves and container are needed. Infusion solution 230, infusion pump 232, analyzer unit 240 and control unit 250 are still provided and are used as described above. Long dwells may be used in which the dialysis fluid is left within patient 212 for a desired duration, e.g., a half-hour. Spent fluid is then pulled, cleaned, stored in the single container 224a, and then returned to patient 212 for another dwell period, and so on. Or, a tidal therapy can be run in which less than all the fluid is removed from the patient, cleaned and returned to the patient on a more regular basis. These more frequent cycles can be of a lesser volume.

It is contemplated in this third PD therapy alternative to size and fill the single container 224a such that the container is larger than the volume of fluid placed in the container by an amount corresponding to an amount of UF that is desired to be removed from the patient or to an amount that is at least known. For example, and referring additionally to FIG. 19, single container 224a could be 1.33 liters in total volume and filled with one liter of fluid, leaving 0.33 liters of room for UF. A 1.33 liter container 224a could be worn by the patient, so that the patient can be ambulatory and functional during treatment. Pump 218 pumps the dialysate fluid from container 224a to the patient 212 and attempts to return all fluid from patient 212 to container 224a plus any UF absorbed in the patient's peritoneum over a corresponding dwell period. Pump 218 can make multiple passes back and forth between container 224a and patient 212.

Figure 19:
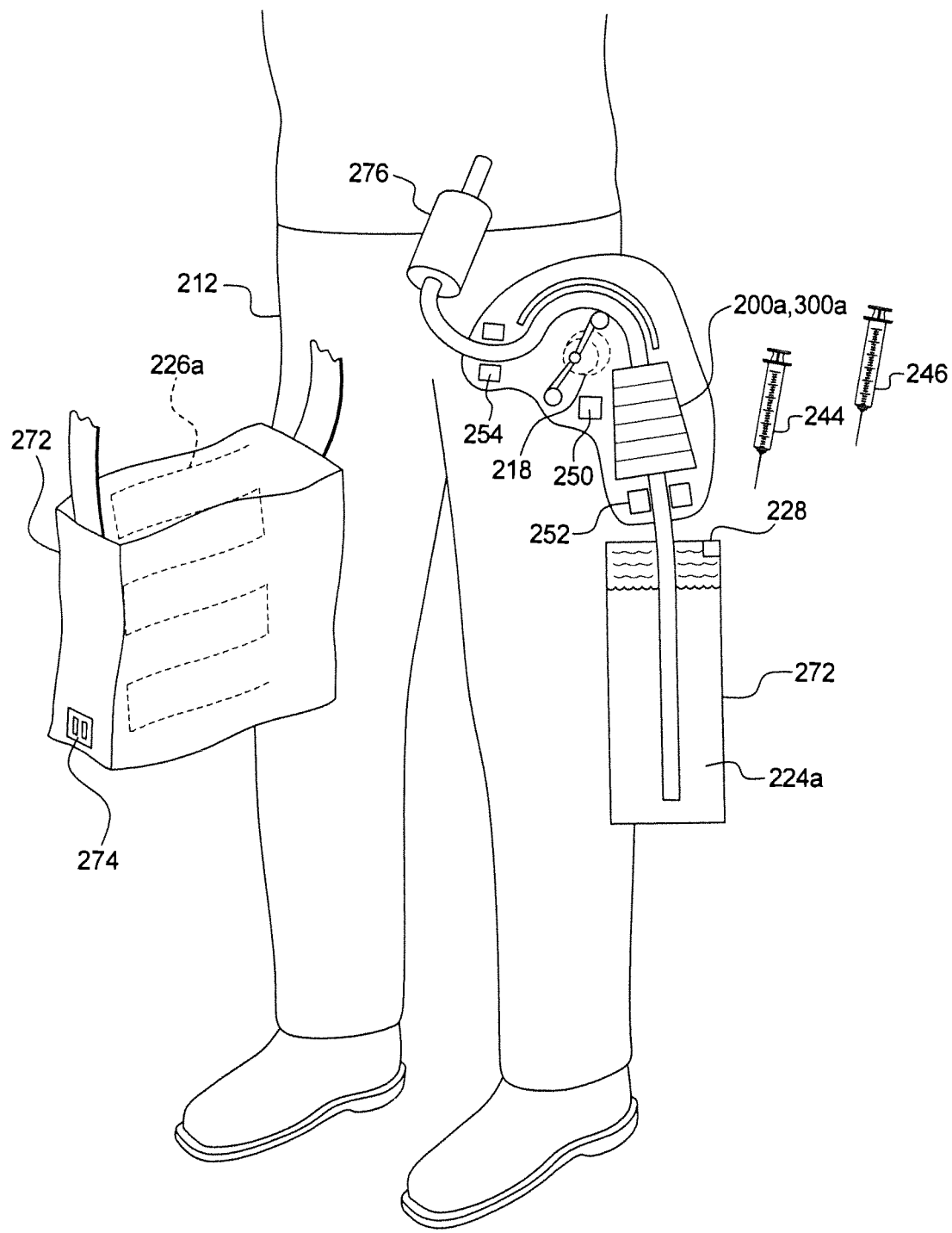

Reusable air sensors 252 and 254, such as ultrasonic sensors, can be placed in operation with the fluid tubing in the positions illustrated in FIG. 16 or FIG. 19 so that it is known when all the fluid has been pumped and air is starting to be drawn. Air sensor 214 is placed so that sorbent cartridge 200a or 300a remains wetted, that is, no air or not much air reaches sorbent cartridge 200a or 300a. So when pump 218 is pumping from container 224a to patient 212, air sensor 252 signals to control unit 250 when to stop pump 218. At that point, the patient's dwell period begins. When pump 218 is pumping instead from patient 212 to container 224a, air sensor 254 signals to control unit 250 when to stop pump 218. Patient drain is considered complete at that point, and pump 218 can reverse itself and fill patient 212 for the next cycle.

Container 224a will hold more and more fluid upon each drain from patient 212 to the container. When container 224a becomes completely full, e.g., holds 1.33 liters of fluid, this PD version of system 210 senses such condition, stops pumping and signals the patient. The sensing can be accomplished by placing a pressure sensor (not illustrated) between flexible container 224a and an outer container (not illustrated), e.g., a rigid or semi-rigid container. When flexible container 224a is not full, the pressure sensor is not contacted and signals (or fails to signal) accordingly. When flexible container 224a is full, the pressure sensor is contacted and signals to control unit 250 to stop pump 218 and inform the patient that container 224a needs to be emptied. The sensing can alternatively be accomplished by placing a current sensor in a power wire leading to a motor (not illustrated) driving the pump actuator of pump 218. For example, if pump 218 is a peristaltic pump driven by a motor, current drawn by a power wire to the motor can be sensed. When container 224a becomes completely full, pressure in line 214 between pump 218 and container 224a builds, causing pump 218 to try to work harder, drawing more current, which is sensed and signaled to control unit 250, which in turn stops pump 218 and informs the patient that container 224a needs to be emptied.

In some embodiments, for example as shown in FIG. 19, a carrying case 272 includes one or more of container 224a, heater 226a, pump 218, control unit 250, sensors 252, 254 and sorbent cartridges 200, 300. Carrying case 272 may include a rechargeable battery 274 that provides power to any or all components housed therein. A PD transfer set 276 may be attached to a patient 212 and to sorbent cartridges 200, 300 to provide a system for performing portable PD therapy.

In an embodiment, container 224a is provided with a pierceable septum 228 that enables the patient to insert a sterilized syringe and needle 244 (FIG. 19) into container 224a and withdraw a known amount of fluid, e.g., 330 milliliters in the above example, to return container 224a to its initial condition. The withdrawn fluid held in the syringe can be expelled to drain or to a drain container. Control unit 250 and pump 218 can then start a new set of multiple passes until container 224a becomes full again, each set of passes resulting in 330 milliliters of UF. Once a total goal of UF is reached, e.g., three sets of passes at 330 milliliters each, leading to a total of about one liter of UF removed, that day's treatment can end. Infusate is added periodically as prescribed by a doctor or clinician using a separate syringe 246 (FIG. 19) and pierceable septum 228. For example, the doctor or clinician may prescribe that 100 milliliters of infusate be delivered to container 224a during the middle or second set of passes. Even if the drain and infusate needles are not perfectly sterilized, sorbent cartridge 200a, 300a will clean the dialysate before being returned to patient 212. Indeed, sorbent cartridge 200a, 300a works to clean the dialysate a first time returning from patient 212 to container 224a (contacting zirconium phosphate first) and a second time when delivered from the container to the patient.

As illustrated in FIGS. 18a and 18b, sorbent cartridge 200, 300, includes a housing having a zirconium phosphate layer followed by at least one of a urease layer, a zirconium oxide layer, a second zirconium phosphate layer (FIG. 18B), and/or a carbon layer. After the initial zirconium phosphate layer, the additional layers can be provided in any combination and in any order. For example, in FIG. 18a, fluid initially contacts zirconium phosphate and then can contact: (i) urease, zirconium oxide, followed by carbon (as illustrated), (ii) urease, carbon, followed by zirconium oxide, (iii) zirconium oxide, carbon, followed by urease, (iv) zirconium oxide, urease, followed by carbon, (v) carbon, zirconium oxide, followed by urease, and (vi) carbon, urease, followed by zirconium oxide. In FIG. 18B, fluid initially contacts zirconium phosphate and then can contact urease, zirconium phosphate (second layer), zirconium oxide, followed by carbon (as illustrated) or twenty-three other combinations, six each for when (i) urease, (ii) zirconium phosphate (second layer), (iii) zirconium oxide, or (iv) carbon is set as the second layer.

In any of the therapies, control unit 250 is configured to cause used dialysis fluid from dialyzer or patient 212 to flow into sorbent cartridge 200, 300 on the initial pass and in a first direction in which the zirconium phosphate layer is the first layer contacted by the dialysis fluid flow before the urease and/or other layers. After the zirconium phosphate layer, the dialysis fluid then passes through, e.g., the urease layer to convert the urea to ammonium. The dialysis fluid can then pass through the zirconium oxide layer and the carbon layer to remove additional electrolytes and waste compounds. After the initial pass through the sorbent cartridge, the dialysis fluid is stored in the storage container 224a, 224b as described above. On the return from storage container 224a, 224b, the dialysis fluid does not have to contact zirconium phosphate initially.

Control unit 250 is further programmed to cause the dialysis fluid to flow in a second direction that is a reverse direction of the first direction, back to the dialyzer 212 (patient et al.). Here, the dialysis fluid from the storage container is passed through sorbent cartridge 200, 300 in the opposite direction from the initial direction. As a result, any ammonium in solution at this time will be absorbed by the zirconium phosphate layer in the sorbent cartridge. Prior to entering the patient or dialyzer 212 and after leaving sorbent cartridge 200, 300, infusion solution 230 can be added to replenish the cleaned dialysis fluid with any necessary electrolytes (e.g., calcium, magnesium, etc.), glucose and to modify the pH of the dialysis fluid (all confirmed by analyzer unit 240) prior being transferred back to the patient or dialyzer 212.

Referring now to FIG. 17, system 310 likewise includes a dialyzer 312 (for hemodialysis and hemodiafiltration). Dialyzer 312 is alternatively a hemofilter for hemofiltration or the patient's peritoneum for peritoneal dialysis. For ease of description, element 312 will be referred to as a dialyzer but includes any of the above. Dialyzer 312 is connected to dialysis fluid lines 314 and 316, which in turn connect fluidly to a recirculation line 318. Recirculation line 318 is connected fluidly to pump 320. Pump 320 can again be a peristaltic pump or membrane pump, the membrane pump including upstream and downstream valves, so that the membrane pump, like the peristaltic pump, is reversible (pump in either direction in line 318 if needed).

Pump 320 pumps to (and from) sorbent cartridge 200, 300 and storage container 324. A heater 326 is provided and illustrated as a batch heater that batch heats containers 324. Heater 326 can are alternatively be an inline heater operating with recirculation line 318.

An infusion solution container 330 is provided. An infusion solution pump 332 (peristaltic or membrane) meters infusion solution from supply 330, through infusion to line 336, selectively via valve V3, to recirculation line 318. Alternatively, infusion solution pump 332 is not provided and a flow restrictor (not illustrated) allows infusion solution to be gravity fed selectively via valves V3 in a metered and controlled manner to line 318.

Dialyzer 312, sorbent cartridge 200, 300 and container 234 can be disposable and part of a disposable set having pump actuation areas operable with the pumps 320 and 332 and valve actuation areas operable with the valves V1 to V4. An analyzer unit 340 through which fluid line 318 extends is reusable, as is control unit 350, heater 326 (and possibly an associated weigh scale), the pump actuators and the valve actuators. Analyzer unit 340 includes probes and sensors, e.g., conductivity sensors, or otherwise samples fluid flowing through line 318 for relevant parameters, such as any one or more of temperature, conductivity, ammonia, ammonium, glucose, electrolyte and pH. Analyzer unit 340 monitors the physical/chemical properties of the dialysis fluid leaving and entering the patient.

The dashed lines are electrical and/or electrical signal lines showing that control unit 350 communicates electrically and operationally with each of the actuators of pumps 320 and 332, the actuators of valves V1 to V4, heater 326 and analyzer unit 340. Control unit 350 includes one or more processor and memory that are programmed, configured and/or manipulated to run a hemodialysis, hemofiltration, hemodiafiltration or peritoneal dialysis sequence. Control unit 350 can likewise include the necessary battery/power components, I/O control for any of the different components of the particular dialysis therapy run on system 310.

For hemodialysis, line 318 is initially primed with dialysate from storage container. Valves V1, V2 and V4 are opened, while valve V3 is closed. Once it is certain that enough dialysate has been pumped to completely fill recirculation line 318, valves V1 and V4 are closed and pump 320 is driven slowly to build pressure in line 318, pushing any air up into the top of container 324. Under normal treatment operation, valve V2 is closed and valves V1 and V4 (and possibly infusate valve V3) are opened. Pump 320 pushes the dialysate counterclockwise in line 318, first through sorbent cartridge 200, 300, then across dialyzer 312 through line 316. Pump 320 pulls used dialysate from dialyzer 312 through line 314. Blood flows from right to left in blood lines 308 and dialyzer 312. Thus, dialysate flow is counter-current to blood flow under normal operation, which is generally considered desirable. Valve V2 is opened periodically to allow UF to be pumped into container 324, where the UF can be weighed by a scale operating with heater 326, the weight recorded by control unit 350.

To reverse dialysate flow through dialyzer 312 for the purpose of flushing the dialyzer to dislodge particles and/or to run therapy in a co-current manner temporarily, it is contemplated to reverse pump 320. Dialysate here is driven in a clockwise direction in line 318 through valves V1 and V4, into and out of dialyzer 312. Therapeutic benefits of providing both counter-current and co-current dialysis are thereby achieved. In an embodiment, pump 320 pumps less than a recirculation circuit 318's volume of dialysate in the reverse clockwise direction, such that the dialysate that is pumped in the reverse direction has been pumped through sorbent cartridge 200, 300 twice, once in the normal direction so that the zirconium phosphate layer is the first to contact the dialysate.

Hemofilatration and hemodilafiltration can be performed alternatively under system 310, which can include valved branching at lines 314 and/or 316, like with system 210. For peritoneal dialysis ("PD"), as with system 210, (i) dialyzer 312 can be used, while blood in lines 308 is replaced with sterile PD fluid, or (ii) dialyzer 312 can be replaced by the patient's peritoneum.

Alternatively for PD, valve V4 is removed from line 316 and line 316 is fed instead into recirculation line 318 (see dotted line). Valve V4 (shown in phantom) is moved to instead be between valve V1 and pump 320 in line 318. Here, with valve V2 closed and moved valve V4 open, spent dialysate from patient 312 can be recirculated around loop 318 and through sorbent cartridge in the counterclockwise direction a plurality of times in a cleaning cycle before valve V2 is opened and valve V4 is closed, driving replenished dialysate into container 324 in a storing cycle. The number of times around recirculation loop 318 is determined by the level of ammonium in the dialysis fluid. Control unit 350 causes a sufficient number of loops to be made, so that the ammonium level is below a threshold level for patient safety (e.g., 20 ppm), e.g., as analyzed by analyzer unit 340. Control unit 350 knows the number of loops made by controlling the timing of valve sequencing and the flow rate of the dialysate in combination with the known volume of recirculation loop plus its inline components, such as sorbent cartridge 200, 300.

The dialysis fluid from the storage container 324 can then be transferred in a treatment cycle back to patient 312 in a clockwise, opposite direction through sorbent cartridge 200, 300. Prior to entering patient 312, infusion solution from source 330 can be used to replenish the cleaned dialysis fluid with the necessary electrolytes (e.g., calcium, magnesium, etc.) glucose to modify the pH of the dialysis fluid appropriately according to analyzer unit 340 before being transferred back to the patient or dialyzer.

Additional Aspects of the Present Disclosure

Aspects of the subject matter described herein may be useful alone or in combination one or more other aspect described herein. Without limiting the foregoing description, in a first aspect of the present disclosure, a dialysis system comprises a sorbent cartridge in fluid communication with at least one of a patient or a dialyzer, the sorbent cartridge including a housing having a zirconium phosphate layer followed by at least one of a urease layer, a zirconium oxide layer, or a carbon layer; a storage container in fluid communication with the sorbent cartridge; a pump in fluid communication with the sorbent cartridge and the storage container; and a control unit in operable communication with the pump, wherein the control unit is programmed to cause the pump to pump a dialysis fluid to flow (i) in a first direction through the sorbent cartridge, wherein the zirconium phosphate layer is contacted by the dialysis fluid before the at least one of the urease layer, zirconium oxide layer or carbon layer and (ii) in a second direction, reverse from the first direction, through the sorbent cartridge wherein the at least one of the urease layer, zirconium oxide layer or carbon layer is contacted by the dialysis fluid before the zirconium phosphate layer.

In accordance with a second aspect of the present disclosure, which may be used with any one or more of the preceding aspects, the dialysis system of is a hemodialysis, hemofiltration, hemodiafiltration or a peritoneal dialysis system.

In accordance with a third aspect of the present disclosure, which may be used with any one or more of the preceding aspects, the dialysis system is configured such that the dialysis fluid is pumped in the first direction, through the sorbent cartridge, to the container.

In accordance with a fourth aspect of the present disclosure, which may be used with any one or more of the preceding aspects, the dialysis system is configured such that the dialysis fluid is pumped in the second direction through the sorbent cartridge to the patient or dialyzer.

In accordance with a fifth aspect of the present disclosure, which may be used with any one or more of the preceding aspects, the dialysis system includes at least one valve located between the storage container and the patient or dialyzer, the control unit further programmed to operate the at least one valve and the pump to perform (i) and (ii).

In accordance with a sixth aspect of the present disclosure, which may be used with any one or more of the preceding aspects, the pump is a reversible pump and the control unit is programmed to reverse the pump to switch from (i) to (ii).

In accordance with a seventh aspect of the present disclosure, which may be used with any one or more of the preceding aspects, the pump is a reversible pump and is a peristaltic pump.

In accordance with a eighth aspect of the present disclosure, which may be used with any one or more of the preceding aspects, the pump is a membrane pump, and includes first and second valves, the first valve located on a first side of the membrane pump, the second valve located on a second side of the membrane pump, the control unit programmed to switch states of the first and second valves in conjunction with the operation of the membrane pump, to perform (i) and (ii).

In accordance with a ninth aspect of the present disclosure, which may be used with any one or more of the preceding aspects, the dialysis system includes a heater, the heater being (a) an inline heater, or (b) a batch heater operable with the storage container.

In accordance with a tenth aspect of the present disclosure, which may be used with any one or more of the preceding aspects, the dialysis system includes an infusion solution, the control unit programmed to cause the infusion solution to be metered into the dialysis fluid during (ii).

In accordance with a eleventh aspect of the present disclosure, which may be used with any one or more of the preceding aspects, the pump is a first pump, and the dialysis system includes a second pump, controlled by the control unit, for metering the infusion solution.

In accordance with a twelfth aspect of the present disclosure, which may be used with any one or more of the preceding aspects, the sorbent cartridge includes a second zirconium phosphate layer.

In accordance with a thirteenth aspect of the present disclosure, which may be used with any one or more of the preceding aspects, the zirconium phosphate layer is a first zirconium phosphate layer, the sorbent cartridge includes a urease layer and a second zirconium phosphate layer, and the control unit is programmed to cause the pump to pump the dialysis fluid to flow (i) in the first direction through the sorbent cartridge, wherein the first zirconium phosphate layer is contacted by the dialysis fluid before the urease layer and the second zirconium phosphate layer and (ii) in the second direction, reverse from the first direction, through the sorbent cartridge wherein the second zirconium phosphate layer and the urease layer are contacted by the dialysis fluid before the first zirconium phosphate layer.

In accordance with a fourteenth aspect of the present disclosure, which may be used with any one or more of the preceding aspects, the sorbent cartridge includes a urease layer followed by at least one of a second zirconium phosphate layer, a zirconium oxide layer, and a carbon layer.

In accordance with a fifteenth aspect of the present disclosure, which may be used with any one or more of the preceding aspects, the sorbent cartridge includes a second zirconium phosphate layer, a urease layer disposed between the zirconium phosphate layer and the second zirconium phosphate layer, a zirconium oxide layer disposed adjacent to the second zirconium phosphate layer, and a carbon layer disposed adjacent to the zirconium oxide layer.

In accordance with a sixteenth aspect of the present disclosure, which may be used with any one or more of the preceding aspects, a method of performing dialysis comprises passing a dialysis fluid in a first flow direction through a sorbent cartridge in fluid communication with at least one of a patient or a dialyzer, the sorbent cartridge including a housing having a zirconium phosphate layer followed by at least one of a urease layer, a zirconium oxide layer, or a carbon layer, wherein the zirconium phosphate layer is first contacted by the dialysis fluid in the first flow direction before the at least one of the urease layer, zirconium oxide layer or carbon layer; storing the dialysis fluid in a storage container; and passing the dialysis fluid from the storage container back through the sorbent cartridge in a reverse flow direction from the first flow direction to reach the patient or the dialyzer.

In accordance with a seventeenth aspect of the present disclosure, which may be used with any one or more of the preceding aspects, the method is used to perform hemodialysis, hemofiltration, hemodiafiltration or peritoneal dialysis.

In accordance with a eighteenth aspect of the present disclosure, which may be used with any one or more of the preceding aspects, the method includes contacting the dialysis fluid with carbon first in the reverse flow direction.

In accordance with a nineteenth aspect of the present disclosure, which may be used with any one or more of the preceding aspects, the method includes contacting the dialysis fluid with urease as a secondary layer in the reverse flow direction.

In accordance with a twentieth aspect of the present disclosure, which may be used with any one or more of the preceding aspects, the method includes contacting the dialysis fluid with zirconium oxide as a secondary layer in the reverse flow direction.

In accordance with a twenty-first aspect of the present disclosure, which may be used with any one or more of the preceding aspects, the zirconium phosphate layer is a first zirconium phosphate layer, and the method includes contacting a second zirconium phosphate layer.

In accordance with a twenty-second aspect of the present disclosure, which may be used with any one or more of the preceding aspects, the housing includes a urease layer disposed between the first and second zirconium phosphate layers.

In accordance with a twenty-third aspect of the present disclosure, which may be used with any one or more of the preceding aspects, the housing includes the first zirconium phosphate layer, followed by the urease layer, followed by the second zirconium phosphate layer.

In accordance with a twenty-fourth aspect of the present disclosure, which may be used with any one or more of the preceding aspects, the housing includes the first zirconium phosphate layer, followed by the urease layer, followed by the second zirconium phosphate layer, followed by a zirconium oxide layer and/or a carbon layer.

In accordance with a twenty-fifth aspect of the present disclosure, which may be used with any one or more of the preceding aspects, the housing includes the first zirconium phosphate layer, followed by the urease layer, followed by the second zirconium phosphate layer, followed by the zirconium oxide layer, followed by the carbon layer.

In accordance with a twenty-sixth aspect of the present disclosure, which may be used with any one or more of the preceding aspects, a dialysis system comprises a sorbent cartridge in fluid communication with at least one of a patient or a dialyzer, the sorbent cartridge including a housing having a zirconium phosphate layer followed by at least one of a urease layer, a zirconium oxide layer, or a carbon layer; a storage container in fluid communication with the sorbent cartridge and the patient or dialyzer; a pump in fluid communication with the sorbent cartridge and the storage container; and a control unit in operable communication with the pump to cause the pump to recirculate a dialysis fluid through the sorbent cartridge in a first direction wherein the zirconium phosphate layer is first contacted by the dialysis fluid before the at least one of the urease layer, zirconium oxide layer or carbon layer for at least two cycles, after which the dialysis fluid is stored in the storage container.

In accordance with a twenty-seventh aspect of the present disclosure, which may be used with any one or more of the preceding aspects, the system is a hemodialysis system, hemofiltration system, hemodiafiltration system or a peritoneal dialysis system.

In accordance with a twenty-eighth aspect of the present disclosure, which may be used with any one or more of the preceding aspects, the control unit is programmed to recirculate the dialysis fluid for a certain amount of time sufficient to complete the at least two cycles.

In accordance with a twenty-ninth aspect of the present disclosure, which may be used with any one or more of the preceding aspects, the control unit is programmed to run the pump at a sufficient flowrate over the sufficient amount of time to complete the at least two cycles.

In accordance with a thirtieth aspect of the present disclosure, which may be used with any one or more of the preceding aspects, the system includes a plurality of valves, the control unit program to operate the plurality of valves and the pump to complete the at least two cycles.

In accordance with a thirty-first aspect of the present disclosure, which may be used with any one or more of the preceding aspects, the control unit further programmed to operate the plurality of valves and the pump to pump to the storage container and pump to the patient or the dialyzer.

In accordance with a thirty-second aspect of the present disclosure, which may be used with any one or more of the preceding aspects, the sorbent cartridge includes a housing having a zirconium phosphate layer, followed by a urease layer, followed by a second zirconium phosphate layer.

In accordance with a thirty-third aspect of the present disclosure, which may be used with any one or more of the preceding aspects, the sorbent cartridge includes a housing having a zirconium phosphate layer followed by a urease layer, followed by a second zirconium phosphate layer, followed by at least one of a zirconium oxide layer and a carbon layer.

In accordance with a thirty-fourth aspect of the present disclosure, which may be used with any one or more of the preceding aspects, the sorbent cartridge includes a housing having a zirconium phosphate layer, followed by a urease layer, followed by a second zirconium phosphate layer, followed by a zirconium oxide layer, followed by a carbon layer.

In accordance with a thirty-fifth aspect of the present disclosure, which may be used with any one or more of the preceding aspects, a method of performing dialysis comprises recirculating a dialysis fluid from a patient or a dialyzer for at least two cycles, each cycle contacting the dialysis fluid first with a zirconium phosphate layer followed by at least one of a urease layer, a zirconium oxide layer, or a carbon layer; storing the recirculated dialysis fluid in a storage container; and transferring the dialysis fluid from the storage container to the patient or the dialyzer.

In accordance with a thirty-sixth aspect of the present disclosure, which may be used with any one or more of the preceding aspects, the method includes operating valves to alternate between a cleaning cycle and a storing cycle.

In accordance with a thirty-seventh aspect of the present disclosure, which may be used with any one or more of the preceding aspects, each cycle of the method includes contacting the dialysis fluid first with a zirconium phosphate layer, followed by a urease layer, followed by at least one of a second zirconium phosphate layer, a zirconium oxide layer, and a carbon layer.

In accordance with a thirty-eighth aspect of the present disclosure, which may be used with any one or more of the preceding aspects, each cycle of the method includes contacting the dialysis fluid first with a zirconium phosphate layer, followed by a urease layer, followed by a second zirconium phosphate layer, followed by a zirconium oxide layer, followed by a carbon layer.

In accordance with a thirty-ninth aspect of the present disclosure, which may be used with any one or more of the preceding aspects, a dialysis system comprises a sorbent cartridge in fluid communication with at least one of a patient or a dialyzer, the sorbent cartridge including a housing having a urease layer followed by a zirconium phosphate layer; a storage container in fluid communication with the sorbent cartridge; a pump in fluid communication with the sorbent cartridge and the storage container; and a control unit in operable communication with the pump, wherein the control unit is programmed to cause the pump to pump a dialysis fluid to flow (i) in a first direction through the sorbent cartridge, wherein the urease layer is contacted by the dialysis fluid before the zirconium phosphate layer and (ii) in a second direction, reverse from the first direction, through the sorbent cartridge wherein the zirconium phosphate layer is contacted by the dialysis fluid before the urease layer.

In accordance with a fortieth aspect of the present disclosure, which may be used with any one or more of the preceding aspects, the dialysis system is a hemodialysis, hemofiltration, hemodiafiltration or a peritoneal dialysis system.

In accordance with a forty-first aspect of the present disclosure, which may be used with any one or more of the preceding aspects, the dialysis system is configured such that the dialysis fluid is pumped in the first direction, through the sorbent cartridge, to the container.

In accordance with a forty-second aspect of the present disclosure, which may be used with any one or more of the preceding aspects, the dialysis system is configured such that the dialysis fluid is pumped in the second direction through the sorbent cartridge to the patient or dialyzer.

In accordance with a forty-third aspect of the present disclosure, which may be used with any one or more of the preceding aspects, the dialysis system includes at least one valve located between the storage container and the patient or dialyzer, the control unit further programmed to operate the at least one valve and the pump to perform (i) and (ii).

In accordance with a forty-fourth aspect of the present disclosure, which may be used with any one or more of the preceding aspects, the pump is a reversible pump and the control unit is programmed to reverse the pump to switch from (i) to (ii).

In accordance with a forty-fifth aspect of the present disclosure, which may be used with any one or more of the preceding aspects, the pump is a reversible pump and is a peristaltic pump.

In accordance with a forty-sixth aspect of the present disclosure, which may be used with any one or more of the preceding aspects, the pump is a membrane pump, and includes first and second valves, the first valve located on a first side of the membrane pump, the second valve located on a second side of the membrane pump, the control unit programmed to switch states of the first and second valves in conjunction with the operation of the membrane pump, to perform (i) and (ii).

In accordance with a forty-seventh aspect of the present disclosure, which may be used with any one or more of the preceding aspects, the dialysis system includes a heater, the heater being (a) an inline heater, or (b) a batch heater operable with the storage container.

In accordance with a forty-eighth aspect of the present disclosure, which may be used with any one or more of the preceding aspects, the dialysis system further includes an infusion solution, and the control unit is programmed to cause the infusion solution to be metered into the dialysis fluid during (ii).

In accordance with a forty-ninth aspect of the present disclosure, which may be used with any one or more of the preceding aspects, the pump is a first pump, and the dialysis system includes a second pump, controlled by the control unit, for metering the infusion solution.

In accordance with a fiftieth aspect of the present disclosure, which may be used with any one or more of the preceding aspects, the sorbent cartridge includes one or more of a zirconium oxide layer, a carbon layer, or a second zirconium phosphate layer.

In accordance with a fifty-first aspect of the present disclosure, which may be used with any one or more of the preceding aspects, the sorbent cartridge does not include a second zirconium phosphate layer.

In accordance with a fifty-second aspect of the present disclosure, which may be used with any one or more of the preceding aspects, the sorbent cartridge does not include a second zirconium phosphate layer on the opposite side of the urease layer as the first zirconium phosphate layer.

In accordance with a fifty-third aspect of the present disclosure, which may be used with any one or more of the preceding aspects, a method of performing dialysis comprises passing a dialysis fluid in a first flow direction through a sorbent cartridge in fluid communication with at least one of a patient or a dialyzer, the sorbent cartridge including a housing having a urease layer followed by a zirconium phosphate layer, wherein the urease layer is first contacted by the dialysis fluid in the first flow direction before the zirconium phosphate layer; storing the dialysis fluid in a storage container; and passing the dialysis fluid from the storage container back through the sorbent cartridge in a reverse flow direction from the first flow direction to reach the patient or the dialyzer.

In accordance with a fifty-fourth aspect of the present disclosure, which may be used with any one or more of the preceding aspects, the method is used to perform hemodialysis, hemofiltration, hemodiafiltration or peritoneal dialysis.

In accordance with a fifty-fifth aspect of the present disclosure, which may be used with any one or more of the preceding aspects, the method includes contacting the dialysis fluid with carbon first in the reverse flow direction.

In accordance with a fifty-sixth aspect of the present disclosure, which may be used with any one or more of the preceding aspects, the method includes contacting the dialysis fluid with urease as a secondary layer in the reverse flow direction.

In accordance with a fifty-seventh aspect of the present disclosure, which may be used with any one or more of the preceding aspects, the method includes contacting the dialysis fluid with zirconium oxide as a secondary layer in the reverse flow direction.

In accordance with a fifty-eighth aspect of the present disclosure, which may be used with any one or more of the preceding aspects, the zirconium phosphate layer is a first zirconium phosphate layer, and the method includes contacting a second zirconium phosphate layer.

In accordance with a fifty-ninth aspect of the present disclosure, which may be used with any one or more of the preceding aspects, the housing includes a urease layer disposed between the first and second zirconium phosphate layers.

In accordance with a sixtieth aspect of the present disclosure, which may be used with any one or more of the preceding aspects, the housing includes the first zirconium phosphate layer, followed by the urease layer, followed by the second zirconium phosphate layer.

In accordance with a sixty-first aspect of the present disclosure, which may be used with any one or more of the preceding aspects, the housing includes the first zirconium phosphate layer, followed by the urease layer, followed by the second zirconium phosphate layer, followed by a zirconium oxide layer and/or a carbon layer.

In accordance with a sixty-second aspect of the present disclosure, which may be used with any one or more of the preceding aspects, the housing includes the first zirconium phosphate layer, followed by the urease layer, followed by the second zirconium phosphate layer, followed by the zirconium oxide layer, followed by the carbon layer.

In accordance with a sixty-third aspect of the present disclosure, which may be used with any one or more of the preceding aspects, a dialysis system comprises a sorbent cartridge in fluid communication with at least one of a patient or a dialyzer, the sorbent cartridge including a housing having a urease layer followed by a zirconium phosphate layer; a storage container in fluid communication with the sorbent cartridge and the patient or dialyzer; a pump in fluid communication with the sorbent cartridge and the storage container; and a control unit in operable communication with the pump to cause the pump to recirculate a dialysis fluid through the sorbent cartridge in a first direction wherein the urease layer is first contacted by the dialysis fluid before the zirconium phosphate layer for at least two cycles, after which the dialysis fluid is stored in the storage container.

In accordance with a sixty-fourth aspect of the present disclosure, which may be used with any one or more of the preceding aspects, the system is a hemodialysis system, hemofiltration system, hemodiafiltration system or a peritoneal dialysis system.

In accordance with a sixty-fifth aspect of the present disclosure, which may be used with any one or more of the preceding aspects, the control unit is programmed to recirculate the dialysis fluid for a certain amount of time sufficient to complete the at least two cycles.

In accordance with a sixty-sixth aspect of the present disclosure, which may be used with any one or more of the preceding aspects, the control unit is programmed to run the pump at a sufficient flowrate over the sufficient amount of time to complete the at least two cycles.

In accordance with a sixty-seventh aspect of the present disclosure, which may be used with any one or more of the preceding aspects, the dialysis system includes a plurality of valves, the control unit program to operate the plurality of valves and the pump to complete the at least two cycles.

In accordance with a sixty-eighth aspect of the present disclosure, which may be used with any one or more of the preceding aspects, the control unit further programmed to operate the plurality of valves and the pump to pump to the storage container and pump to the patient or the dialyzer.

In accordance with a sixty-ninth aspect of the present disclosure, which may be used with any one or more of the preceding aspects, the sorbent cartridge includes a housing having a urease layer, followed by a zirconium phosphate layer, followed by a second zirconium phosphate layer.

In accordance with a seventieth aspect of the present disclosure, which may be used with any one or more of the preceding aspects, the sorbent cartridge includes a housing having a urease layer followed by a zirconium phosphate layer, followed by at least one of a zirconium oxide layer and a carbon layer.

In accordance with a seventy-first aspect of the present disclosure, which may be used with any one or more of the preceding aspects, the sorbent cartridge includes a housing having a urease layer, followed by a zirconium phosphate layer, followed by a zirconium oxide layer, followed by a carbon layer.

In accordance with a seventy-second aspect of the present disclosure, which may be used with any one or more of the preceding aspects, the sorbent cartridge does not include a second zirconium phosphate layer.

In accordance with a seventy-third aspect of the present disclosure, which may be used with any one or more of the preceding aspects, the sorbent cartridge does not include a second zirconium phosphate layer on the opposite side of the urease layer as the first zirconium phosphate layer.

In accordance with a seventy-fourth aspect of the present disclosure, which may be used with any one or more of the preceding aspects, a method of performing dialysis comprises recirculating a dialysis fluid from a patient or a dialyzer for at least two cycles, each cycle contacting the dialysis fluid first with a urease layer followed by a zirconium phosphate layer; storing the recirculated dialysis fluid in a storage container; and transferring the dialysis fluid from the storage container to the patient or the dialyzer.

In accordance with a seventy-fifth aspect of the present disclosure, which may be used with any one or more of the preceding aspects, the method includes operating valves to alternate between a cleaning cycle and a storing cycle.

In accordance with a seventy-sixth aspect of the present disclosure, which may be used with any one or more of the preceding aspects, each cycle of the method includes contacting the dialysis fluid first with a urease layer, followed by a zirconium phosphate layer, followed by at least one of a second zirconium phosphate layer, a zirconium oxide layer, and a carbon layer.

In accordance with a seventy-seventh aspect of the present disclosure, which may be used with any one or more of the preceding aspects, each cycle of the method includes contacting the dialysis fluid first with a urease layer, followed by a zirconium phosphate layer, followed by a second zirconium phosphate layer, followed by a zirconium oxide layer, followed by a carbon layer.

In accordance with a seventy-eighth aspect of the present disclosure, any of the structure and functionality illustrated and described in connection with FIG. 1 may be used in combination with any one or more of the preceding aspects.

In accordance with a seventy-ninth aspect of the present disclosure, any of the structure and functionality illustrated and described in connection with FIG. 2 may be used in combination with any one or more of the preceding aspects.

In accordance with an eightieth aspect of the present disclosure, any of the structure and functionality illustrated and described in connection with FIG. 5 may be used in combination with any one or more of the preceding aspects.

In accordance with an eighty-first aspect of the present disclosure, any of the structure and functionality illustrated and described in connection with FIG. 6 may be used in combination with any one or more of the preceding aspects.

In accordance with an eighty-second aspect of the present disclosure, any of the structure and functionality illustrated and described in connection with FIG. 7 may be used in combination with any one or more of the preceding aspects.

In accordance with an eighty-third aspect of the present disclosure, any of the structure and functionality illustrated and described in connection with FIG. 11 may be used in combination with any one or more of the preceding aspects.

In accordance with an eighty-fourth aspect of the present disclosure, any of the structure and functionality illustrated and described in connection with FIG. 12A may be used in combination with any one or more of the preceding aspects.

In accordance with an eighty-fifth aspect of the present disclosure, any of the structure and functionality illustrated and described in connection with FIG. 12B may be used in combination with any one or more of the preceding aspects.

In accordance with an eighty-sixth aspect of the present disclosure, any of the structure and functionality illustrated and described in connection with FIG. 12C may be used in combination with any one or more of the preceding aspects.

In accordance with an eighty-seventh aspect of the present disclosure, any of the structure and functionality illustrated and described in connection with FIG. 16 may be used in combination with any one or more of the preceding aspects.

In accordance with an eighty-eighth aspect of the present disclosure, any of the structure and functionality illustrated and described in connection with FIG. 17 may be used in combination with any one or more of the preceding aspects.

In accordance with an eighty-ninth aspect of the present disclosure, any of the structure and functionality illustrated and described in connection with FIG. 18A may be used in combination with any one or more of the preceding aspects.

In accordance with a ninetieth aspect of the present disclosure, any of the structure and functionality illustrated and described in connection with FIG. 18B may be used in combination with any one or more of the preceding aspects.

In accordance with a ninety-first aspect of the present disclosure, any of the structure and functionality illustrated and described in connection with FIG. 19 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of performing dialysis comprising:
passing a dialysis fluid in a first flow direction through a sorbent cartridge in fluid communication with at least one of a patient or a dialyzer, the sorbent cartridge including a housing having a urease layer followed by a zirconium phosphate layer, wherein the urease layer is first contacted by the dialysis fluid in the first flow direction before the zirconium phosphate layer;
storing the dialysis fluid in a storage container; and
passing the dialysis fluid from the storage container back through the sorbent cartridge in a reverse flow direction from the first flow direction to reach the patient or the dialyzer.

2. The method of claim 1, wherein the method is used to perform hemodialysis, hemofiltration, hemodiafiltration or peritoneal dialysis.

3. The dialysis method of claim 1, which includes contacting the dialysis fluid with carbon first in the reverse flow direction.

4. The dialysis method of claim 1, which includes contacting the dialysis fluid with urease as a secondary layer in the reverse flow direction.

5. The dialysis method of claim 1, wherein the housing further includes a zirconium oxide layer, and wherein the method includes contacting the dialysis fluid with the zirconium oxide layer prior to the urease layer in the reverse flow direction.

6. The dialysis method of claim 1, wherein the zirconium phosphate layer is a first zirconium phosphate layer, and which includes contacting a second zirconium phosphate layer.

7. The dialysis method of claim 6, wherein the housing includes the urease layer disposed between the first and second zirconium phosphate layers.

8. The dialysis method of claim 7, wherein the housing includes the second zirconium phosphate layer, followed by the urease layer, followed by the first zirconium phosphate layer in the first flow direction.

9. The dialysis method of claim 8, wherein the housing includes the second zirconium phosphate layer, followed by the urease layer, followed by the first zirconium phosphate layer, followed by a zirconium oxide layer and/or a carbon layer in the first flow direction.

10. The dialysis method of claim 9, wherein the housing includes the second zirconium phosphate layer, followed by the urease layer, followed by the first zirconium phosphate layer, followed by the zirconium oxide layer, and followed by the carbon layer in the first flow direction.

\* \* \* \* \*